(12) United States Patent
Careaga et al.

(10) Patent No.: US 11,994,514 B2
(45) Date of Patent: May 28, 2024

(54) METHOD OF DETERMINING SEPSIS IN THE PRESENCE OF BLAST FLAGGING

(71) Applicant: Beckman Coulter, Inc., Brea, CA (US)

(72) Inventors: Diana B. Careaga, Miami, FL (US); Robert T. Magari, Cooper City, FL (US); Liliana M. Tejidor, Coral Gables, FL (US); Nicole Carpio, Tampa, FL (US)

(73) Assignee: Beckman Coulter, Inc., Brea, CA (US)

( * ) Notice: Subject to any disclaimer, the term of this patent is extended or adjusted under 35 U.S.C. 154(b) by 1138 days.

(21) Appl. No.: 16/390,597

(22) Filed: Apr. 22, 2019

(65) Prior Publication Data

US 2019/0383800 A1 Dec. 19, 2019

Related U.S. Application Data

(60) Provisional application No. 62/685,753, filed on Jun. 15, 2018.

(51) Int. Cl.
G01N 33/50 (2006.01)
A61B 5/00 (2006.01)
(Continued)

(52) U.S. Cl.
CPC ......... *G01N 33/5094* (2013.01); *A61B 5/412* (2013.01); *G01N 15/1031* (2013.01);
(Continued)

(58) Field of Classification Search
CPC .............. A61B 5/412; G01N 15/0656; G01N 15/1031; G01N 2015/008;
(Continued)

(56) References Cited

U.S. PATENT DOCUMENTS 5,125,737 A 7/1992 Rodriquez et al.
5,341,291 A 8/1994 Roizen, III et al.
(Continued)

FOREIGN PATENT DOCUMENTS

CN 102033035 B 11/2013
EP 1021701 7/2000
(Continued)

OTHER PUBLICATIONS

Beckman Coulter, Early Sepsis Indicator (ESId) Application for UniCel DxH 900 Series with System Manager Software, PN C26693AC (Jun. 2019), https://www.beckmancoulter.com/download/file/wsr-308328/C26693AC?type=pdf (Year: 2019).*
(Continued)

*Primary Examiner* — Dean Kwak
(74) *Attorney, Agent, or Firm* — Frost Brown Todd LLP

(57) ABSTRACT

Embodiments of the present disclosure may allow for an efficient and accurate way or system to assess whether an individual has sepsis, including an individual who may exhibit symptoms or clinical criteria similar to inflammation. Embodiments include using a laboratory test that may be routinely ordered. Embodiments of the present invention may allow for the diagnosis of sepsis even when some cells show an abnormal size. Often, when white blood cells show a likelihood of an abnormal size, a "blast flag" in a system is triggered to warn a user that the sample may warrant further analysis. Unexpectedly, the diagnosis of sepsis status using standard deviation of monocyte volume may be more accurate when considering whether a blast flag has been triggered. Based on the sepsis status, treatment may be started quickly, thereby preventing complications, including organ failure and death, of not treating sepsis fast enough.

13 Claims, 17 Drawing Sheets

(51) Int. Cl.
  *G01N 15/01* (2024.01)
  *G01N 15/1031* (2024.01)
  *G01N 15/14* (2006.01)
  *G01N 33/487* (2006.01)
  *G01N 33/49* (2006.01)
  *G01N 33/569* (2006.01)
  *G16H 10/40* (2018.01)
  *G01N 15/06* (2006.01)

(52) U.S. Cl.
  CPC ....... *G01N 33/48735* (2013.01); *G01N 33/49* (2013.01); *G01N 33/5091* (2013.01); *G01N 33/56972* (2013.01); *G16H 10/40* (2018.01); *G01N 2015/016* (2024.01); *G01N 15/0656* (2013.01); *G01N 2015/1402* (2013.01); *G01N 2800/26* (2013.01)

(58) Field of Classification Search
  CPC ....... G01N 2015/1402; G01N 2800/26; G01N 33/48735; G01N 33/49; G01N 33/5091; G01N 33/5094; G01N 33/56972; G16H 10/40
  See application file for complete search history.

(56) References Cited

U.S. PATENT DOCUMENTS

| | | | |
|---|---|---|---|
| 5,529,933 | A | 6/1996 | Young et al. |
| 6,228,652 | B1 | 5/2001 | Rodriquez et al. |
| 6,509,192 | B1 | 1/2003 | Young |
| 7,109,036 | B2 | 9/2006 | Ortiz et al. |
| 7,135,341 | B2 | 11/2006 | Ortiz et al. |
| 7,176,031 | B2 | 2/2007 | Li et al. |
| 7,195,919 | B2 | 3/2007 | Jacobs et al. |
| 7,285,417 | B2 | 10/2007 | Ortiz et al. |
| 7,390,662 | B2 | 6/2008 | Riley et al. |
| 7,393,688 | B2 | 7/2008 | Ortiz et al. |
| 8,094,299 | B2 | 1/2012 | Wells et al. |
| 8,189,187 | B2 | 5/2012 | Graham et al. |
| 8,221,995 | B2 | 7/2012 | Lee et al. |
| 8,719,053 | B2 | 5/2014 | Showalter et al. |
| 9,939,453 | B2 | 4/2018 | Lu et al. |
| 10,221,453 | B2 | 3/2019 | Shi et al. |
| 2001/0051879 | A1 | 12/2001 | Johnson et al. |
| 2001/0051880 | A1 | 12/2001 | Schurenberg et al. |
| 2003/0105648 | A1 | 6/2003 | Schurenberg et al. |
| 2004/0042471 | A1 | 3/2004 | Yung et al. |
| 2004/0220761 | A1 | 11/2004 | Yundt-Pacheco |
| 2004/0267562 | A1 | 12/2004 | Fuhrer et al. |
| 2005/0022103 | A1 | 1/2005 | Yundt-Pacheco |
| 2005/0159982 | A1 | 7/2005 | Showalter et al. |
| 2008/0186134 | A1 | 8/2008 | Parkhurst et al. |
| 2009/0149724 | A1 | 6/2009 | Mark et al. |
| 2011/0046910 | A1 | 2/2011 | Haas et al. |
| 2011/0076685 | A1 | 3/2011 | Moeller et al. |
| 2011/0166794 | A1 | 7/2011 | Linssen et al. |
| 2012/0109531 | A1 | 5/2012 | Knafel et al. |
| 2012/0109682 | A1 | 5/2012 | Seltzer et al. |
| 2013/0197943 | A1 | 8/2013 | Conlin et al. |
| 2013/0246079 | A1 | 9/2013 | Hoffman et al. |
| 2014/0084930 | A1 | 6/2014 | Han |
| 2014/0160464 | A1 | 6/2014 | Han |
| 2014/0172321 | A1 | 6/2014 | Han |
| 2015/0338427 | A1 | 11/2015 | Pollack et al. |
| 2016/0168638 | A1 | 6/2016 | Garrett et al. |
| 2016/0356801 | A1 | 12/2016 | Glavina et al. |
| 2017/0285624 | A1 | 10/2017 | Lesher |
| 2019/0128906 | A1 | 5/2019 | Ramirez et al. |
| 2019/0324035 | A1 | 10/2019 | Magari et al. |
| 2019/0324036 | A1 | 10/2019 | Xin et al. |
| 2019/0348182 | A1 | 11/2019 | Magari et al. |
| 2019/0362824 | A1 | 11/2019 | Xin et al. |
| 2021/0007675 | A1 | 1/2021 | Tejidor et al. |
| 2021/0010924 | A1 | 1/2021 | Tejidor et al. |
| 2021/0011005 | A1 | 1/2021 | Tejidor et al. |

FOREIGN PATENT DOCUMENTS

| | | | |
|---|---|---|---|
| EP | 1718966 | 11/2006 | |
| JP | 2012-529033 A | 11/2012 | |
| KR | 20150036329 A | 4/2015 | |
| KR | 20150091049 A | 8/2015 | |
| WO | WO 88/07198 A1 | 9/1988 | |
| WO | WO 2004/044556 A2 | 5/2004 | |
| WO | WO 2012/139047 A2 | 10/2012 | |
| WO | WO 2014/028534 A2 | 2/2014 | |
| WO | 2014/084930 | 6/2014 | |
| WO | WO 2014/154810 A1 | 10/2014 | |
| WO | WO 2017/132132 | 8/2017 | |
| WO | WO-2017132132 A1 * | 8/2017 | ............ G16H 10/40 |
| WO | WO 2019/028448 A1 | 2/2019 | |

OTHER PUBLICATIONS

Beckman Coulter, UniCel DxH Series with System Manager Software, PN B26647AG (Apr. 2020), https://www.beckmancoulter.com/download/file/wsr-156667/B26647AG?type=pdf (Year: 2020).*

FDA 510(k) Substantial Equivalence Determination Decision Summary, https://www.accessdata.fda.gov/cdrh_docs/reviews/K181599.pdf (Year: 2018).*

Beckman Coulter, Early Sepsis Indicator (ESId) Application Addendum, UniCel DxH 900 Series with System Manager Software Coulter Cellular Analysis System, PN C42014AC (Apr. 2020), https://www.beckmancoulter.com/download/file/wsr-292218/C42014AC?type=pdf (Year: 2020).*

"Biomarker," The Pharmaceutical Society of Japan, a pharmaceutical science glossary, 2008, 2 pgs.

"Red Blood Cell Distribution With (RDW): Definition and Calculation—LabCE.com, Laboratory Continuing Education," Nov. 2012, downloaded Aug. 22, 2019 from: https://labce.com/spg579122_red_blood_cell_distribution_width_rdw_definition_a.aspx, 1 pg.

Sukhacheva, et al., "The Role of Monocytes in the Progression of Sepsis," Beckman Coulter, 2018, downloaded Aug. 22, 2019 from: media.beckmancoulter.com/-/media/diagnostics/products/hematology/early-sepsis-indicator/docs/role-of-monocytes-for-progression-of-sepsis-en.pdf, 12 pgs.

Zhou, et al., "VCS parameters of neutrophils, monocytes and lymphocytes may indicate local bacterial infection in cancer patients who accepted cytotoxic chemotherapeutics," Eur J Clin Microbiol Infect Dis, 2016, 35:41-48, 8 pgs.

Zonneveld, R., et al., "Analyzing Neutrophil Morphology, Mechanics, and Motility in Sepsis: Options and Challenges for Novel Bedside Technologies," Crit Care Med, 2016, 44(1):218-228, 11 pgs.

European Examination Report dated Oct. 15, 2020 for Application No. EP 17704357.7, 10 pgs.

International Search Report and Written Opinion dated Aug. 23, 2019 for International Application No. PCT/US2019/028488, 10 pgs.

International Search Report and Written Opinion dated Oct. 20, 2020 for International Application No. PCT/US2020/041535, 12 pgs.

International Search Report and Written Opinion dated Oct. 8, 2020 for International Application No. PCT/US2020/041548, 10 pgs.

International Search Report and Written Opinion dated Oct. 5, 2020 for International Application No. PCT/US2020/041541, 10 pgs.

Japanese Office Action, Notice of Reasons for Refusal, dated Oct. 29, 2020 JP 2018-538892, 27 pgs.

U.S. Office Action, Restriction Requirement, dated Apr. 7, 2021 for U.S. Appl. No. 15/987,541, 5 pgs.

U.S. Office Action, Non-Final Rejection, dated Jul. 31, 2020 for U.S. Appl. No. 16/073,757, 23 pgs.

U.S. Office Action, Notice of Allowance, dated Feb. 8, 2021 for U.S. Appl. No. 16/073,757, 20 pgs.

Aird; William C., "The Hematologic System as a Marker of Organ Dysfunction in Sepsis", Mayo Clin Proc., Jul. 2003; 78:869-881, *2003 Mayo Foundation for Medical Education and Research.*

(56) References Cited

OTHER PUBLICATIONS

Anonymous, "Multiple Logistic Regression Analysis", Jan. 17, 2013, retrieved from http://sphweb.bumc.cu.edu/otlt/MPH-Modules/8S/8S704_Multivariable/8S704_Multivariables8.html.
Bhargava, et al. "Elevated mean neutrophil volume+ CRP is a highly sensitive and specific predictor of neonatal sepsis", Letter to the Editor, International Journal of Laboratory Hematology, DOI: 10.1111/iijh.12120, 2013, 4 pages.
Celik, et al., "Automated determination of neutrophil VCS parameters in diagnosis and treatment efficacy of neonatal sepsis", Pediatric Research, vol. 71, No. 1, Jan. 2012, pp. 121-125.
Chaves, et al. "Neutrophil Volume Distribution Width: A New Automated Hematologic Parameter for Acute Infection", Arch Pathol Lab Med, vol. 130. Mar. 2006, pp. 378-380.
Chaves, et al. Quantitative Determination of Neutrophil VCS Parameters by the Coulter Automated Hematology Analyzer: New and Reliable Indicators for Acute Bacterial Infection. American Journal Clinical Pathology, 2005, 124:440-444, DOI, 10.1309/LLF75WOFWQQ8TCC5.
Cho, et al., "Biomarkers of Sepsis", Infection & Chemotherapy, Feb. 2014; 46:1-12.
Crouser, et al., "Improved Early Detection of Sepsis in the ED with a Novel Monocyte Distribution Width Biomarker", 152#3 Chest, Sep. 2017, pp. 518-526.
Dellinger, et al. "Surviving Sepsis Campaign: International Guidelines for Management of Severe Sepsis and Septic Shock, 2012", Intensive Care Medicine, 2013, 39:164-228, DOI 10.1007/s00134-012-2769-8.
Dilmoula, et al., "Volume, Conductivity and Scatter Properties of Leukocytes (VCS Technology) in Detecting Sepsis in Critically Ill Adult Patients", Blood (ASH annual Meeting Abstracts) 2011; 118: Abstract 4729, 3 pages.
Early Sepsis Indicator Application Addendum UniCel DxH 900 Coulter Cellular Analysis System, Beckman Coulter, published Version: v1, Available online at: https://www.analis.be/site/objects/media/0/0/8/1/9/0081990_media/media1 .pdf, Apr. 26, 2018, 38 pages.
Ferrer, et al., "Emperic Antibiotic Treatment Reduces Mortality in Severe Sepsis and Septic Shock From the First Hour: Results From a Guideline-Based Performance Improvement Program", Critical Care Medicine, Aug. 2014, vol. 42, No. 8, pp. 1749-1755.
Gaieski, et al., "Impact of time to antibiotics on survival in patients with severe sepsis or septic shock in whom early goal-directed therapy was initiated in the emergency department", Critical Care Medicine, 2010, vol. 38, No. 4, pp. 1045-1053.
Garnacho-Montero, et al., "Impact of adequate empirical antibiotic therapy on the outcome of patients admitted to the intensive care unit with sepsis", Critical Care Medicine, 2003;31 :2742-51.
Gea-Banecloche, et al. "Sepsis associated with immunosuppressive medications: An evidence-based review" Critical Care Medicine 2004;32:S578-S590.
Glickman, et al., Disease Progression in Hemodynamically Stable Patients Presenting to the Emergency Department With Sepsis. Academic Emergency Medicine, vol. 17, Issue 4, Apr. 2, 2010, pp. 383-390.
Hou, et al., Viral infection triggers rapid differentiation of human blood monocytes into dendritic cells, *Blood*, Mar. 29, 2012, vol. 119, No. 12, pp. 3128-3132.
Lee, et al., "Mean cell vols. of neutrophils and monocytes are promising markers of sepsis in elderly patients", Blood Research, vol. 48, No. 3, Sep. 2013, 5 pages.
Levy, et al., "2001 SCCM/ESICM/ACCP/ATS/SIS Sepsis Definitions Conference", Critical Care Medicine, Mar. 28, 2003, 29: 530-538.
Liu, et al., "Hospital Deaths in Patients with Sepsis from 2 Independent Cohorts", *JAMA* Jul. 2, 2014; 312: 90-92.
Mardi, et al., Mean cell volume of neutrophils and monocytes compared with C-reactive protein, interleukin-6 and white blood cell count for prediction of sepsis and nonsystemic bacterial infections, accepted for publication, Sep. 23, 2009, International Journal of Laboratory Hematology 2010;32:410-418.
Park, et al, "Screening of sepsis using leukocyte cell population data from the Coulter automatic blood cell analyzer DxH800", International Journal of Laboratory Hematology, Dec. 6, 2010, 9 pages.
Raimondi, et al., "Automated Determination of Neutrophil Volume as Screening Test for Late-Onset Sepsis in Very Low Birth Infants", Pediatric Infectious Disease Journal, Feb. 2010;29:288-89.
Seymour, et al. "Severe Sepsis in Pre-Hospital Emergency Care: Analysis of Incidence, Care, and Outcome", American Journal of Respiratory Critical Care Medicine, Dec. 15, 2012; 186:1264-71.
Shalova, et al., "Human Monocytes Undergo Functional Reprogramming during Sepsis Mediated by Hypozia- Inducible Factor-1a", Immunity, Mar. 17, 2015; 42:484-98.
Skibsted, et al., "Bench-to-bedside review: Future novel diagnostics for sepsis—a systems biology approach", Critical Care Oct. 4, 2013;17:231, 15 pages.
Torio, et al., "National Inpatient Hospital Costs: The Most Expensive Conditions by Payer, 2011", H-CUP US, Aug. 2013, 8 pages, retrieved from: https://www.hcup-us.ahrq.gov/reports/statbriefs/sb160.jsp.
"UniCel DxH 800—Coulter Cellular Analysis System", Available online at: https://www.udh.med.sa/advices/DxH_operator_Manual.pdf, Aug. 5, 2017, 54 pages.
Vis, et al., "Verification and Quality Control of Routine Hematology Analyzers", International Journal of Laboratory Hematology, vol. 38, No. 1, May 9, 2016, pp. 100-109.
Kaukonen et al., "Systemic Inflammatory Response Syndrome Criteria in 30 Defining Severe Sepsis," New England J of Med, 372: 1629-38 (2015) (doi:610.1056/NEJMoaI415236).
Singer et al., "The Third International Consensus Definitions for Sepsis and Septic Shock (Sepsis-3)," JAMA, 10 315(8):801-810 (2016) (doi: 10.1001/jama.2016.0287).
Goyette et al., "Hematologic changes in sepsis and their therapeutic implications," Seminars in Respiratory and Critical Care Medicine, vol. 25, No. 6, pp. 645-659 (2004).
Warner, "Tips for evaluating a peripheral blood smear for possible sepsis," (2014) available at laboratory manager.advanceweb.com/signs-of-sepsis/.
International Search Report and Written Opinion dated Aug. 20, 2019 for International Application No. PCT/US2019/031151, 9 pages.
International Search Report and Written Opinion dated Apr. 20, 2017 for International Application No. PCT/US2017/014708, 16 pages.
International Search Report and Written Opinion dated Mar. 26, 2019 for International Application No. PCT/US2018/057645, 16 pages.
International Search Report and Written Opinion dated Aug. 2, 2019 for International Application No. PCT/US2019/028487, 7 pages.
International Search Report and Written Opinion dated Sep. 4, 2019 for International Application No. PCT/US2019/028486, 11 pages.
International Search Report and Written Opinion dated May 4, 2018 for International Application No. PCT/US2018/020087, 13 pages.
U.S. Appl. No. 16/488,503, entitled "Cross Discipline Disease Management System," filed Aug. 23, 2019.
Beckman Coulter, "Coulter® 3-D VCS Technology," from <http://www.cyto.purdue.edu/cdroms/cyto2/6/coulter/ ss000125.htnn> (Year: 1996).
Cembrowski, George S., B. Smith, and D. Tung. "Rationale for using insensitive quality control rules for today's hematology analyzers." *International Journal of Laboratory Hematology* 32.6p2 (2010): 606-615.
Nachimuthu, Senthil K., and Peter J. Haug. "Early detection of sepsis in the emergency department using Dynamic Bayesian Networks." *AMIA Annual Symposium Proceedings*. vol. 2012. American Medical Informatics Association, 2012.
Petrak, Russel M., et al. "The value of an infectious diseases specialist." *Clinical infectious diseases* 36.8 (2003): 1013-1017.
Chinese Office Action dated May 31, 2021, for Application No. 201780006733.8, 14 pages.
Chinese Office Action dated Mar. 9, 2022, for Application No. 201780006733.8, 4 pages.

(56) References Cited

OTHER PUBLICATIONS

European Examination Report dated Nov. 27, 2020, for Application No. 18712041.5, 11 pages.
European Examination Report dated Jul. 12, 2022, for Application No. 18845383.1, 13 pages.
Indian Office Action dated Jun. 25, 2021, for Application No. 201817031635, 7 pages.
Japanese Notification of Reasons for Refusal dated Feb. 4, 2022, for Application No. 2021-012832, 4 pages.
Japanese Notification of Reasons for Refusal dated Jun. 17, 2022, for Application No. 2021-012832, 2 pages.
Korean Office Action dated Aug. 27, 2021, for Application No. 10-2018-7024386, 27 pages.
U.S. Non-Final Rejection dated Jul. 9, 2021, for U.S. Appl. No. 15/987,541, 15 pages.
U.S. Final Rejection dated Feb. 17, 2022, for U.S. Appl. No. 15/987,541, 14 pages.
U.S. Notice of Allowance dated Sep. 1, 2022, for U.S. Appl. No. 15/987,541, 8 pages.
U.S. Restriction Requirement dated May 2, 2022, for U.S. Appl. No. 16/170,389, 7 pages.
U.S. Non-Final Rejection dated Aug. 1, 2022, for U.S. Appl. No. 16/170,389, 21 pages.
U.S. Non-Final Rejection dated Jul. 2, 2021, for U.S. Appl. No. 16/390,633, 9 pages.
U.S. Non-Final Rejection dated Feb. 25, 2022, for U.S. Appl. No. 16/390,633, 13 pages.
U.S. Final Rejection dated Aug. 9, 2022, for U.S. Appl. No. 16/390,633, 11 pages.
U.S. Non-Final Rejection dated Jul. 9, 2021, for U.S. Appl. No. 16/390,648, 15 pages.
U.S. Final Rejection dated Feb. 17, 2022, for U.S. Appl. No. 16/390,648, 14 pages.
U.S. Notice of Allowance dated Jun. 15, 2022, for U.S. Appl. No. 16/390,648, 7 pages.
U.S. Restriction Requirement dated Jun. 16, 2021, for U.S. Appl. No. 16/488,503, 8 pages.
U.S. Non-Final Rejection dated Nov. 24, 2021, for U.S. Appl. No. 16/488,503, 21 pages.
U.S. Final Rejection dated Aug. 11, 2022, for U.S. Appl. No. 16/488,503, 21 pages.
U.S. Non-Final Rejection dated Jun. 23, 2022, for U.S. Appl. No. 16/925,933, 9 pages.
U.S. Restriction Requirement dated Aug. 8, 2022, for U.S. Appl. No. 16/925,937, 13 pages.
U.S. Restriction Requirement dated Oct. 5, 2022, for U.S. Appl. No. 16/925,943, 8 pages.

* cited by examiner

METHOD OF DETERMINING SEPSIS IN THE PRESENCE OF BLAST FLAGGING

CROSS-REFERENCES TO RELATED APPLICATIONS

This application is a nonprovisional of and claims the benefit of priority to U.S. Provisional Patent Application No. 62/685,753, filed Jun. 15, 2018, entitled "METHOD OF DETECTING SEPSIS IN THE PRESENCE OF BLAST FLAGGING," the entire contents of which are herein incorporated by reference.

This application is related by subject matter to PCT Patent Application No. PCT/US17/14708, titled "Infection Detection and Differentiation Systems and Methods," filed Jan. 24, 2017, which claims the benefit of U.S. Provisional Patent Application No. 62/288,091, titled "Infection Detection and Differentiation Systems and Methods," filed Jan. 28, 2016. This application is also related to U.S. Provisional Application No. 62/660,795, titled "Sepsis Infection Detection Systems and Methods," filed Apr. 20, 2018. The contents of these applications are incorporated herein by reference for all purposes.

BACKGROUND

Sepsis is an uncontrolled systemic inflammatory response to infection that may rapidly progress to a life-threatening condition that can lead to shock and organ failure (i.e., septic shock and severe sepsis) if not treated immediately. A patient admitted to a medical facility may show clinical features of systemic inflammation. A medical professional may then attempt to determine if the inflammation is caused by an infection, leading to a diagnosis of sepsis, or some other causes, leading to a diagnosis of systemic inflammatory response syndrome (SIRS). In some cases, a patient may have no obvious signs of systemic inflammation, which may mean that the patient may not be considered at risk for sepsis.

If undetected, sepsis may lead to severe sepsis or septic shock, which has a mortality rate of about 60%. A large fraction of hospital deaths are associated with sepsis. Diagnosing sepsis is challenging because of the lack of an accurate biomarker. Additionally, clinical criteria that may indicate sepsis, such as hypothermia, hyperthermia, tachycardia, tachypnea, may not distinguish sepsis from SIRS or other conditions. These criteria may be associated with non-infectious etiologies that may be present in a hospital emergency room, including trauma, burns, pancreatitis, sickle cell crisis, and other inflammatory disorders. These similarities between sepsis and inflammation may make diagnosing sepsis challenging and time-consuming. For example, obtaining blood culture results to confirm an infection and/or identify a pathogen responsible for the infection may take several days. During the time it takes to complete conventional diagnostic testing, the patient's condition could deteriorate, possibly to a degree that the patient requires extraordinary clinical support or can no longer be treated effectively. For these and additional reasons, improved or new systems and methods for assessing the likelihood of systemic infection, including sepsis, are desired.

BRIEF SUMMARY

Sepsis, or the likelihood of developing sepsis in the near term, may be assessed in part by evaluating the monocyte distribution width (MDW) measured from a blood sample. In particular, elevated MDW values may be associated with sepsis or the onset of sepsis. Exemplary methods are disclosed, for example, in PCT Patent Application No. PCT/US17/14708 and U.S. Provisional Application No. 62/660,795. At the time those methods were developed, it was expected that certain kinds of patients, including, without limitation, patients on a chemotherapy or immunosuppression therapy, trauma patients, burn patients, and leukemia patients could not be assessed for sepsis or onset of sepsis using MDW. Such patients' conditions involve a proliferation of immature cells, called "blasts." As used herein, "blasts" include neutroblasts, lymphoblasts, monoblasts, and myeloblasts (immature granulocytes). While other blasts may be present in a peripheral blood sample, the blasts measured as part of the monocyte distribution are predominantly lymphoblasts, monoblasts, and myeloblasts. As a point of reference, and without limitation, blasts in a healthy, adult human might comprise less than 1%, or even less than 0.3%, of the mononuclear leukocytes in a peripheral blood sample. In many examples, anything above 1% in blood may be considered suspicious and positive for blasts. For comparison, some kinds of leukemia may be associated with blast populations of between about 1-30% of the mononuclear leukocytes in a peripheral blood sample.

Blasts tend to be larger than more mature cells, so a proliferation of blasts would be expected to increase the MDW observed relative to a blood sample with fewer blasts. That is, patients with a proliferation of blasts, such as patients on a chemotherapy or immunosuppression therapy, trauma patients, burn patients, and leukemia patients, would be expected to have an elevated baseline monocyte distribution width relative to a baseline measure for a "normal" patient without blast proliferation. As such, an elevated baseline MDW measurement was expected to interfere with a sepsis evaluation based on MDW.

An automated hematology analyzer may "flag" blood analysis results that are consistent with blast proliferation. The flag indicates that something about the cellular analysis indicated the presence of a blast population. The blasts could be identified using a variety of techniques, including, without limitation, preferential staining techniques, size-sorting of cells, internal or surface cell morphology evaluation, surface biomarker(s) on the cells, and the like. These techniques are known in the art, as are the production of blast flags in automated hematology analyzers.

In an automated hematology analyzer, different cell types can be identified based on a variety of known technologies. For example, cells may be differentiated based on size, surface morphology, internal morphology, conductivity, volume, light scatter, selective staining, surface biomarkers, image analysis, and the like. Because some cells have similar or overlapping features, combinations of cell features may be used to classify the cells. For white blood cells, a 5-part differential can identify monocytes, lymphocytes, neutrophils, eosinophils and basophils, for example, by plotting cell volume, cell light absorbance, light scatter and/or conductivity in combinations. Exemplary scatterplots are illustrated by FIG. 14, showing on example of a comparison between non-septic and septic patients. Different cell populations cluster in different parts of the scatterplots, and particular cells can be classified according to the cluster with which cluster they most closely associate. Depending on the cell classification technique(s) used, blasts may appear as a separate population of cells, as a sub-cluster or sub-population of cells, or the presence of blasts may be inferred from unusual patterns within the expected classifications, such as increased variation in the data for one or more cell types, increased range for the data for one or more cell types, decreased separation of different cell types, or combinations thereof. It is not unusual for biological samples to show variation and imperfect segmentation. However, if these patterns exceed a pre-determined threshold, an automated hematology analyzer may provide a message or "flag," indicating that the sample varies from expected segmentation in a manner consistent with the presence of blasts. For the purpose of this analysis, a blast population may be significant based on statistical deviation from expected classification patterns, rather than clinical significance of the presence or prevalence of the blasts. For example, the blast population may be deemed significant by an automated hematology analyzer based on an estimated count or proportion of blasts, based on deviation from the expected classification patterns without attempting to quantify the number of blasts, or both. The degree of statistical deviation required to identify the sample as including an atypical number of blasts will differ based on the classification technique(s) used. It may also vary based on the policies or preferences of a particular laboratory or hospital. For samples identified as having a significant blast content, follow-up may include flow cytometry, manual and/or automated imaging to confirm and/or quantify the presence of blasts.

Because a blast flag indicates blast proliferation, and because blast proliferation increases MDW, it was expected that patients with blast flags could not be assessed for sepsis or onset of sepsis using MDW as a test parameter, because the elevated baseline MDW associated with the blast flag would not permit discrimination of septic and non-septic patients based on elevated MDW. In the case of a blast flag, the expectation was that it would not be possible to distinguish the elevated MDW associated with blast proliferation from an elevated MDW observed in sepsis or onset of sepsis.

As described below, it has surprisingly been discovered that MDW can be used to distinguish septic from non-septic patients in the presence of a blast flag. As used herein, a septic patient is one with an out of control inflammatory/immune response based on a collection of symptoms that can have multiple causes across patients or for a single patient. In fact, the same thresholds could be used to evaluate sepsis and onset of sepsis in patients with and without blast flags. However, as described in more detail below, the number of false positive results for patients with blast flags can be reduced by employing a higher threshold for evaluating sepsis or sepsis onset in patients with a blast flag, to improve the specificity of the sepsis evaluation for this sub-population.

Embodiments of the present disclosure may allow for an efficient and accurate way to assess whether an individual has sepsis or may develop sepsis or a severe infection, including an individual who may experiencing blast proliferation. Embodiments include using a laboratory test that may be routinely ordered. Individuals to be tested may be in an emergency room. Systems and methods to assess the likelihood of sepsis may have a sensitivity and specificity above the currently recognized standard of care values of 0.60 to 0.70. Embodiments of the present invention may allow for the diagnosis of sepsis even in the presence of a blast flag. Often, when analysis shows a pre-determined likelihood of a blast population in a patient sample, a "blast flag" in a system is triggered to warn a user that the sample may warrant further analysis. The additional analysis could include re-analyzing the sample to confirm that the result was not caused by sampling bias, or could include review of the sample by a trained pathologist, or could include review of the clinical record for the patient or further patient examination to consider possible causes of blast proliferation, or any combination thereof. Embodiments of the present disclosure relate to the ability to identify sepsis (or the potential development of sepsis) even in the presence of immature blasts of various lineages. In a specific example, this identification may occur even in the presence of monoblasts that would otherwise interfere with the ability to measure monocyte distribution width (MDW).

Embodiments of the present invention improve upon diagnostic, biological, and medical related technologies or technical fields by providing a fast, simple, and accurate determination of the sepsis status. Based on the sepsis status, treatment may be started quickly, thereby preventing complications, including organ failure and death, of not treating sepsis fast enough. The sepsis status may include an indication that the patient is at high risk of developing sepsis, rather than a diagnosis of sepsis. For patients with a blast flag, the sepsis status may be helpful in distinguishing between septic infection and a symptom associated with the underlying condition or disease. This might be useful, for example, for patients on a chemotherapy regimen, where it is important to determine whether a fever is caused by septic or pre-septic infection, inflammation, invasive procedures, drug reactions, tumor growth, or other, possibly unidentified, factors. A chemotherapy patient who presents with a fever may be advised to delay chemotherapy growth on the assumption that the fever is caused by infection, however, delaying chemotherapy may be undesirable if the fever is actually caused by tumor growth or other non-infectious causes. This is just one example of the utility of MDW for distinguishing sepsis or pre-septic infection from underlying conditions, in particular hematological malignancies with the presence of blasts in blood.

The sepsis status may indicate sepsis is determined in the blood sample or that sepsis is likely to develop based on characteristics measured in the blood sample. Sepsis being likely in the blood sample may indicate that a treatment for sepsis in the individual is recommended or needed. Sepsis results from an uncontrolled systemic response to an infection. Sepsis may result from any infection in the body. For example, a simple skin infection may trigger a septic event. A post-surgical infection may lead to sepsis as the post-surgical infection may include infection and system inflammation. Predicting which infections may result in a septic event is difficult and not always possible. Clinicians desire an early detection or indication that a patient may become septic.

Embodiments of the present technology may include an automated method for evaluating sepsis status associated with a blood sample from an individual. The method may include determining a standard deviation of monocyte volume associated with the blood sample. The method may also include determining a value of a parameter associated with the blood sample. The parameter may indicate a likelihood of a white blood cell in the blood sample having a blast proliferation that is statistically different from an expected distribution of white blood cells. The method may further include comparing the value of the parameter to a first cutoff value to provide a first comparison. In addition, the method may include determining a second cutoff value based on the first comparison. The method may further include comparing the standard deviation of monocyte volume to the second cutoff value to provide a second comparison. Based on the second comparison, the method may include evaluating the sepsis status associated with the blood sample.

Embodiments of the present technology may further include an automated method for evaluating a sepsis status associated with a blood sample obtained from an individual, the method comprising: determining a standard deviation of monocyte volume associated with the blood sample; determining a blast population characteristic associated with the blood sample; comparing the value of the blast population characteristic associated with the blood sample to a first cutoff value to provide a first comparison; determining a second cutoff value based on the first comparison; comparing the standard deviation of monocyte volume to the second cutoff value to provide a second comparison; and evaluating the sepsis status associated with the blood sample based on the second comparison. In one example, the blast population characteristic is a binary indicator of the presence or absence of a significant number of blasts. In the same or a different example, the blast population is identified based on the size of the blasts relative to other white blood cells.

Embodiments may include an automated system for evaluating a sepsis status associated with a blood sample obtained from an individual. The system may include a first module that includes an electrode assembly configured to measure direct current (DC) impedance of cells of the blood sample passing individually through a cell interrogation zone. The system may also include a data processing module in connectivity with the first module. The data processing module may include a processor and a tangible non-transitory computer readable medium. The tangible non-transitory computer readable medium may be programmed with a computer application that, when executed by the processor, cause the processor to determine a standard deviation of monocyte volume associated with the blood sample using the DC impedance of cells measured in the first module. The processor may further be caused to determine a value of a parameter associated with the blood sample using the DC impedance of cells measured in the first module. The parameter may indicate a likelihood of a white blood cell in the blood sample having a blast proliferation that is statistically different from an expected distribution of white blood cells. The processor may further be caused to compare the value of the parameter to a first cutoff value to provide a first comparison. The processor may also be caused to determine a second cutoff value based on the first comparison. In addition, the processor may be caused to compare the standard deviation of monocyte volume to the second cutoff value to provide a second comparison. Furthermore, the processor may be caused to evaluate the sepsis status associated with the blood sample based on the second comparison.

A better understanding of the nature and advantages of embodiments of the present invention may be gained with reference to the following detailed description and the accompanying drawings.

DETAILED DESCRIPTION

Figure 1A:
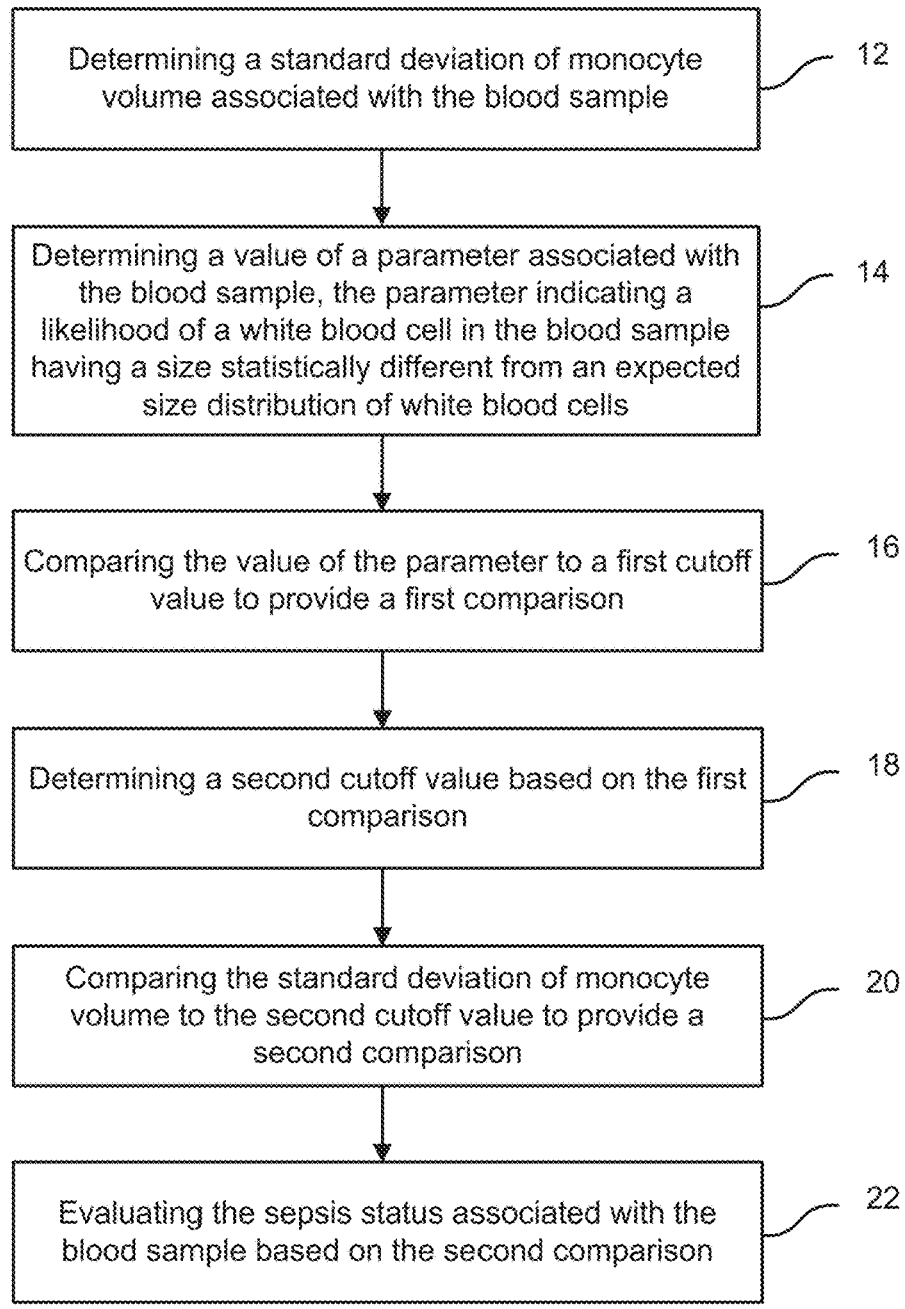
FIG. 1A is a block flow diagram of an automated method for evaluating the sepsis status associated with a blood sample from an individual, according to embodiments of the present invention.

Diagnostic markers for sepsis have been researched for many years. Even so, there has not been a clear diagnostic test or biomarker for determining sepsis available. It was previously believed that a series of seven blood-cell-related factors could be reviewed in order to determine possible septic infection. See, for example, Park et al., "Screening of sepsis using leukocyte cell population data from the Coulter automatic blood cell analyzer DxH800," International Journal of Laboratory Hematology, 2011, 33, 391-399 at 397-98. As recently as a few years ago, it was believed that parameters or indices based on a calculation including at least two of the seven factors were needed in order to make a septic infection prediction. The present inventors have determined that, rather than requiring a formula to calculate a parameter or index using the parameters, onset of a possible septic infection can be predicted through simple and efficient comparison to cutoff values. These comparisons may include using the standard deviation of monocyte volume, which may still be used to evaluate sepsis even when a non-infectious condition has resulted in an elevated baseline measure for an individual's standard deviation of monocyte volume. Indeed, consideration of whether white blood cells show an abnormal blast proliferation unexpectedly increases the accuracy or precision in evaluating sepsis. In other words, using the standard deviation of monocyte volume to evaluate sepsis is unexpectedly improved in accuracy or precision when certain white blood cells with an abnormal blast proliferation (or other parameters) are present (or absent).

Embodiments of the present invention thus include systems and methods that assess the likelihood of infection, including sepsis, in a patient using cell count and cell population data. Data about the cell population, such as the standard deviation of the monocyte volume or monocyte distribution width (MDW) may be compared to a cutoff value for determining if an individual has sepsis or is developing sepsis or if there is a suspicion of the patient having sepsis. Data about the white blood cell (WBC) count may then be used as a secondary check to the initial determination/testing. Evaluation of MDW sequentially with WBC (before or after, but as distinct, binary evaluations), may provide a clinical indicator with sensitivity and specificity about 0.80 or more. In a specific example, MDW and WBC data are reviewed together as part of the same test.

The definition of sepsis itself has changed, illustrating additional difficulties in conclusively diagnosing sepsis. Under the Sepsis-2 definition, sepsis was defined based on systemic inflammatory response syndrome (SIRS) criteria. SIRS may refer to a clinical syndrome that results from a dysregulated inflammatory response to a noninfectious insult, such as an autoimmune disorder, pancreatitis, vasculitis, thromboembolism, burns, or surgery. SIRS criteria include temperature, heart rate, respiratory rate, and white blood cell count. SIRS criteria are described in Kaukonen et al., "Systemic Inflammatory Response Syndrome Criteria in Defining Severe Sepsis," *New England J. of Med.*, 372: 1629-38 (2015) (doi: 10.1056/NEJMoa1415236) and the Supplementary Appendix, the contents of both of which are incorporated herein by reference for all purposes. "Sepsis" may be the clinical syndrome that results from a dysregulated inflammatory response to an infection. Under Sepsis-2, sepsis includes two SIRS criteria and infection. "Severe sepsis" may refer to sepsis-induced tissue hypoperfusion or organ dysfunction resulting from infection. "Septic shock" may refer to a condition of severe sepsis plus hypotension persisting despite adequate fluid resuscitation, which may be defined as infusion of 20-30 mL/kg of crystalloids.

In 2016, Sepsis-3 updated the definition of sepsis, which is described in Singer et al., "The Third International Consensus Definitions for Sepsis and Septic Shock (Sepsis-3)," *JAMA*, 315(8):801-810 (2016) (doi: 10.1001/jama.2016.0287). Sepsis-3 defines sepsis as a life-threatening organ dysfunction caused by a dysregulated host response to infection. Organ dysfunction can be identified using a Sequential [Sepsis-related] Organ Failure Assessment (SOFA) score. The SOFA "score grades abnormality by organ system and accounts for clinical interventions." "Septic shock" is considered a subset of sepsis, when "underlying circulatory and cellular/metabolic abnormalities are profound enough to substantially increase mortality." There is no "severe sepsis" in Sepsis-3. As Sepsis-2 and Sepsis-3 definitions are not identical, even defining "sepsis" is challenging. Nonetheless, certain patient sample measurements, alone or in combination, may identify patients who meet the criteria for Sepsis-2 and/or Sepsis-3, or are at elevated risk of meeting the criteria for Sepsis-2 and/or Sepsis-3 in the near future (e.g., within 24 hours, or within 48 hours, of sample testing), as described herein.

As sepsis is defined based on a set of clinical signs and symptoms, sepsis is not detectable in the blood the way a parasite or a low hemoglobin concentration may be detected. Methods and systems described herein may enable a clinician to identify or determine sepsis when clinical conditions are vague or non-specific (e.g., flu-like symptoms, which may be symptoms of sepsis). If "detecting" or a form of the word is used herein with sepsis, the term should be understood to mean determining, diagnosing, or assessing sepsis, rather than measuring a specific component definitively indicating sepsis.

Conventional systems and methods for diagnosing sepsis may be inefficient and/or time consuming. In current practice, clinical criteria may be used to diagnose sepsis by detecting systemic inflammation that accompanies sepsis. The clinical criteria, however, may be common to both sepsis and SIRS, which may be associated with non-infectious conditions. An individual who may have sepsis may undergo laboratory tests, including but not limited to a test to generate a complete blood count (CBC) with differential (CBC-diff); measurements of C-reactive protein (CRP), serum lactate, erythrocyte sedimentation rate (ESR), and Procalcitonin (PCT); and cultures for bacteria. These technologies may result in poor sensitivity and/or specificity when used to diagnose sepsis. Other systems and methods may be limited to leukocyte cell population data (CPD) and may still be lacking in sensitivity and/or specificity. Some conventional methods may use CPD parameter(s) (e.g., monocyte volume) that lack the sensitivity and/or specificity of CPD parameters used herein. In some cases, conventional methods may require the use of multiple CPD parameters to show an increased sensitivity or specificity. Some of these tests may be expensive and may not be run routinely on individuals, and as a result, individuals who are infected and potentially septic but not yet symptomatic may not be diagnosed promptly or not diagnosed at all. The lack of an efficient and accurate method and system to evaluate the infection status may lead to a clinician administering antibiotics as a precautionary measure, resulting in overuse of antibiotics. Adverse drug events, adverse treatment interactions or side effects that might be easily managed in a healthy patient can present significant problems in a patient with SIRS, sepsis or similarly severe clinical conditions. Medicating all potentially septic patients with antibiotics, therefore, is not an ideal clinical strategy.

On the other hand, waiting for test results may endanger an individual's life. Analyzing a blood culture to definitively diagnose sepsis may take two to four days. In that time, an individual can develop sepsis, develop organ failure, be past the point of recovery, and eventually die. A quick and accurate method to evaluate sepsis would improve patient outcomes and save lives. Any time saved in identifying sepsis or potential sepsis may improve patient outcomes. By one estimate, a septic patient's chance of recovery decreases by 7%-8% for every hour of delay in treatment of the underlying infection.

Other tests may also be inadequate. CRP may not be specific to bacterial and viral infections. Serum lactate may not be specific to sepsis and may be used more as a prognostic biomarker in sepsis instead of a diagnostic biomarker. ESR may represent physical properties associated with inflammatory processes but has poor specificity for infection. Blood cultures may be too time consuming to allow physicians to make immediate or timely treatment decisions. Additionally, antibiotic drugs and/or fastidious pathogens may limit the sensitivity of blood cultures. PCT, lacking sufficient sensitivity and specificity in symptomatic patients, may not reliably differentiate sepsis from other non-infectious causes of SIRS in critically ill patients. Furthermore, because PCT may be a separate test that may be performed only upon clinician request, the test may not be administered early and may not be an early identifier of septic patients.

Conventional systems may include computers, which are not able to evaluate the infection status with sufficient sensitivity and specificity even if the computer had all the information provided from a blood sample. Embodiments of the present invention may improve computer-related technology by allowing the computer to perform evaluation of the infection status, including the evaluation of a sepsis status. Embodiments of the present invention may also decrease programming complexity, processing power requirements, storage requirements, and bandwidth requirements. Memory need to store instructions and to store parameters may be reduced. Embodiments of the present invention may not include computational complexity beyond a determination of cell population data parameters in the sample and a comparison of two numbers, thereby increasing computational efficiency and lowering cost.

Embodiments of the present invention include comparing the standard deviation of monocyte volume (SD-V-MO) to a cutoff value, which depends on whether a white blood cell has an abnormal size. White blood cells having an abnormal size in a blood sample may occur when immature white blood cells are in the blood instead of in the bone marrow. Abnormally sized white blood cells in the blood may be an indication of leukemia, a compromised immune system, or trauma. There are three types of white blood cells that can vary in morphology and/or size, including monocytes, lymphocytes, or neutrophils. In some instances, these cells may have an abnormal size. The standard deviation of each type of cell (e.g., monocyte volume) is specific for that type of cell variation. Thus, the standard deviation should be related only to that type of abnormally-sized cell. As a result, using a parameter indicating a the presence of blasts would not be expected to improve sensitivity and specificity for evaluating sepsis based on the standard deviation of that specific type of cell (e.g. monocyte) volume.

Embodiments of the present invention may evaluate the sepsis status. The sepsis status may indicate that an individual has sepsis. If an individual is evaluated to have sepsis, clinical criteria may be used to confirm whether the individual has sepsis. Clinical criteria may include heart rate, body temperature, presence of a fever, and mental status. Individuals diagnosed with sepsis may receive closer monitoring, hospital admission, aggressive IV fluids, repeated blood cultures, vitamin (e.g. vitamin C) treatment, and/or prioritized diagnoses and treatment.

I. EXAMPLE METHODS

As shown in FIG. 1A, embodiments of the present technology may include an automated method 1 for evaluating sepsis status associated with a blood sample from an individual. The individual may be at risk of sepsis, may have leukemia, or may have a compromised immune system. The blood sample may be obtained from the individual using a syringe or any suitable instrument using accepted medical protocols. A physician, nurse, or other medical professional may obtain the blood sample from the individual.

At block 12, method 1 may include determining a standard deviation of monocyte volume associate with the blood sample. The standard deviation of monocyte volume may also be called the monocyte distribution width (MDW). In some embodiments, a measure of statistical variance of the monocyte volume may be used in place of the standard deviation of monocyte volume.

The standard deviation of monocyte volume may be determined using a first module. Method 1 may include delivering a hydrodynamically focused stream of the blood sample toward a cell interrogation zone of an optical element of the first module. Method 1 may also include measuring, with an electrode assembly, current (DC) impedance of cells of the blood sample passing individually through the cell interrogation zone. Determining the standard deviation of monocyte volume may be based on the measured DC impedance of cells of the blood sample.

At block 14, method 1 may also include determining a value of a parameter associated with the blood sample. The parameter may indicate a presence of blasts in the peripheral blood. The parameter may be a characteristic of the white blood cells in the blood sample. The parameter may be derived from a count or proportion of blasts based on size and/or volume, or on morphological characteristics of a sample of cells from the blood sample, or on surface properties of a sample of cells from the blood sample, or from light scatter analysis of a sample of cells from the blood sample, or a combination thereof. The parameter may be a blast population characteristic.

The parameter may be a binary parameter. For example, the parameter may have a first value when there likelihood of a number or proportion of blasts in a blood sample exceeds a pre-established threshold. The parameter may have a second value when the likelihood a number or proportion of blasts in a blood sample does not exceed a pre-established threshold. The first value may be different from the second value. The first value may be 1, and the second value may be 0. In other embodiments, the first value may be a message or a string that there is a likelihood of an abnormal white blood cell, and the second value may be a message or string that there is not a likelihood of an abnormal white blood cell. The likelihood may be a 40%, 50%, 60%, 70%, 80%, 85%, 90%, 95%, or 99% probability that a number or proportion of blasts in a blood sample exceeds a pre-established threshold.

The binary parameter may be the "blast flag" used with certain systems, including the Coulter automatic blood cell analyzer DxH800 and DxH900. The blast flag in these systems may be a warning that patterns exceed a predetermined threshold, and the automated hematology analyzer may provide a message or "flag," indicating that the sample varies from expected segmentation in a manner consistent with the presence of blasts. Blasts can represent a mixed population of cells often associated with specimen abnormalities that alter the white cell population's pattern distribution in data plots and histograms away from a normal differential pattern of distribution. The presence of blast cells may trigger other available suspect messages. Not all blood samples that contain blasts may report a suspect message. The sensitivity and specificity of the blast flag may be adjusted on a blood cell analyzer so that the blast flag warning may appear less or more often or in response to different parameters or combinations of parameters associated with the blood sample.

In some embodiments, the parameter may not be a binary parameter. A higher value of the parameter may indicate a higher likelihood. For example, a maximum value of the parameter may indicate a 100% likelihood of a number or proportion of blasts in a blood sample exceeding a pre-established threshold. The value of the parameter may be proportional to the percent likelihood. The maximum value may be 1 or 100%.

In one example, a blast suspect message flag may be triggered when the algorithm detects the presence of an abnormal population based on VCS technology in a particular size as detected by volume and the maturity of the cell (because blasts are immature and have less complexity to the cell); therefore, the scatter properties as detected by Light Scatter is less.

At block 16, method 1 may further include comparing the value of the parameter to a first cutoff value to provide a first comparison. For example, the cutoff value may be read as a "yes/no" for presence of a blast flag. If there are blasts (yes), a high MDW cut-off may be used. If there are not blasts (no), a second, lower MDW cut-off may be used. The first cutoff value may be equal to one of the two possible values for the parameter. For example, the first cutoff value may be 1 or a message string (e.g., "Yes"). With a binary parameter, the first comparison may be whether the parameter matches the first cutoff value. If the parameter is not a binary parameter, the first cutoff value may be a value corresponding to a certain likelihood of the white blood cell in the blood sample having a blast proliferation that is statistically different from an expected distribution of white blood cells. The first cutoff value may be a value between the minimum value for the parameter (e.g., 0) and the maximum value for the parameter (e.g., 1). The first cutoff value may be selected for a certain probability that a cell is of abnormal size. For example, the first cutoff value may be a 40%, 50%, 60%, 70%, 80%, 85%, 90%, 95%, or 99% probability that the blood sample reflects the presence of blasts.

At block 18, method 1 may include determining a second cutoff value based on the first comparison. The second cutoff value may be higher when the value of the parameter is greater than or equal to the first cutoff value than when the value of the parameter is not greater than the first cutoff value. For example, the second cutoff value may be higher when the parameter indicates a likelihood of blast proliferation (e.g., blast flag is present).

The second cutoff value may be one of two possible cutoff values, one with a greater value than the other. If the value of the parameter is determined to be greater than or equal to the first cutoff value, then the second cutoff value may be determined to be the greater of the two possible cutoff values. If the value of the parameter is determined to be not greater than or equal to the first cutoff value, then the second cutoff value may be determined to be the lesser of the two possible cutoff values. In other words, if a likelihood of blast proliferation exceeds a pre-established threshold, then the second cutoff value will be greater than otherwise.

The higher cutoff value for the second cutoff value may be in a range from 26 to 36, including from 26 to 28, from 28 to 30, from 30 to 32, from 32 to 34, or from 34 to 36. The lower cutoff value for the second cutoff value may be in a range from 19 to 23, including from 19 to 21, from 19 to 20, from 20 to 21, from 21 to 22, or from 22 to 23.

In some embodiments, the second cutoff value may not be based on the first comparison. Method 1 may include receiving data that the individual has a proliferation of blasts. The data may not be determined from the blood sample. The patient's medical record may indicate the patient has an acute, chronic or terminal condition known to cause blast proliferation. The individual may be known to suffer from leukemia or from a compromised immune system. An individual known to have abnormal blast proliferation, or likely to have abnormal blast proliferation, or to have leukemia may result in the second cutoff value being the higher of possible cutoff values. In embodiments where the parameter is not a binary parameter, the additional data that the individual has abnormal blast proliferation may be used with data obtained from the blood sample. The additional data not from the blood sample may be used to increase value of the parameter to reflect a higher likelihood or to decrease the first cutoff value.

At block 20, method 1 may further include comparing the standard deviation of monocyte volume to the second cutoff value to provide a second comparison. The comparison may include determining whether the standard deviation of monocyte volume is less than, greater than, or equal to the second cutoff value.

At block 22, method 1 may include evaluating the sepsis status associated with the blood sample based on the second comparison. The sepsis status may be evaluated as indicating suspicion of sepsis if the standard deviation of monocyte volume is greater than the second cutoff value. Suspicion of sepsis may mean that sepsis is present in the individual or that the individual is at risk of developing sepsis, including that the risk is high enough to warrant preventative treatment for sepsis. The sepsis status may be evaluated as not indicating suspicion of sepsis if the standard deviation of monocyte volume is not greater than the second cutoff value. In some embodiments, evaluating the sepsis status of the blood sample of the individual may include predicting whether the individual has sepsis, assessing the likelihood of the individual having sepsis, or determining whether the individual has sepsis.

Methods of evaluating the sepsis status may have a specificity for sepsis greater than 0.55. The specificity may describe the ability of the test to correctly identify those patients without the disease or condition. The specificity may be 0.55 or higher, 0.60 or higher, 0.65 or higher, 0.70 or higher, 0.75 or higher, 0.80 or higher, 0.85 or higher, 0.90 or higher, or 0.95 or higher in embodiments. The area under the curve (AUC) in a receiver operating characteristic (ROC) curve may be 0.79 or higher, 0.82 or higher, 0.85 or higher, 0.89 or higher, 0.90 or higher, 0.91 or higher, 0.92 or higher, 0.93 or higher, 0.94 or higher, 0.95 or higher, 0.96 or higher, 0.97 or higher, 0.98 or higher, or 0.99 or higher in embodiments.

Methods of evaluating the sepsis status may have a sensitivity for sepsis greater than 0.55. The sensitivity may describe the ability of a diagnostic test to correctly identify those patients with the disease or condition. A false negative may describe when the method indicates that the blood status shows no infection when in fact infection is present. The sensitivity may be 0.55 or higher, 0.60 or higher, 0.65 or higher, 0.70 or higher, 0.75 or higher, 0.80 or higher, 0.85 or higher, 0.90 or higher, or 0.95 or higher in embodiments.

In some embodiments, method 1 may include determining a white blood cell count (WBC) associated with the blood sample. Method 1 may further include comparing WBC to a threshold value to provide a third comparison. The threshold value may be a value from 3,000 cells/μL to 15,000 cells/μL, including 3,000, 4,000, 5,000, 10,000, 11,000, 12,000, 13,000, 14,000, or 15,000 cells/μL. In one specific example, the threshold WBC value may be less than about 4,000 cells/μL or greater than about 12,000 cells/μL. Comparing WBC to a threshold value may include determining whether WBC exceeds the threshold value. Exceeding the threshold value may mean being either greater than the threshold value or being less than the threshold value. For example, if the threshold value is 4,000 cells/μL, exceeding the threshold value may mean that the white blood cell count is less than 4,000 cells/μL. If the threshold value is 12,000 cells/μL, exceeding the threshold value may mean that the white blood cell count is greater than 12,000 cells/μL. Evaluating the sepsis status may be based on the second comparison and the third comparison.

The reason exceeding the threshold value may be either greater than or less than the threshold value is that the threshold value may represent one end of a range of normal values for white blood cell count. For example, a normal white blood cell count may be from 4,000 to 12,000 cells/µL. The range may be from any count described herein to any other count described herein. A white blood cell count outside the threshold range may indicate a potential for sepsis. Accordingly, the automated method may also include comparing to a second threshold value, the second threshold value being the other end of a range of values as the threshold value. So if the normal range for WBC is between 4,000 to 12,000 cells/µL and a threshold value is set at 4,000 cells/µL, then a value that is less than 4,000 cells/µL would increase suspicion of sepsis. If a threshold value is set a 12,000 cells/µL, then a value that is greater than 12,000 cells/µL would also increase suspicion of sepsis. In both cases, the abnormal WBC value increases suspicion of sepsis in the context of an MDW value above or below the MDW value threshold cutoff. These threshold values may be set by the testing institution based on patient population demographics. Additionally, the range considered normal might be expanded or reduced in order to favor errors that tend to produce false negatives or errors that tend to produce false positives, respectively, based on the desired risk profile, clinical context and/or analytical context for the evaluation. The reasoning may be that, due to the extreme health threat posed, it is better to mistakenly identify many false positives than to miss a positive detection due to thresholds that are set too narrowly.

The automated method may further include evaluating that the sepsis status is that the blood sample does not indicate sepsis upon determining the standard deviation of the monocyte volume does not exceed the second cutoff value and/or upon determining the white blood cell count does not exceed the threshold value. In addition, the automated method may include evaluating that the sepsis status is that the blood sample indicates sepsis upon determining the standard deviation of the monocyte volume exceeds the second cutoff value and upon determining the white blood cell count exceeds the threshold value.

The method may also exclude using a biomarker for sepsis. For example, sepsis has no known, reliable biomarker. Even if sepsis did have a reliable biomarker, embodiments described herein may be used to decide whether to run a biomarker test on a patient, or might be used before a biomarker reaches peak expression in the course of the immune dysregulation associated with sepsis, or might be used if the biomarker is subject to interference or inconsistent interpretation (e.g., the biomarker is associated with patient conditions other than sepsis, even if those conditions are rare). However, as described above, a biomarker may be used to identify, isolate and/or enumerate different kinds of cells in a blood sample, without using a biomarker specific to sepsis.

The second cutoff value or the threshold value may be calculated by maximizing an estimated value of sensitivity for an infection for a given value of specificity for sepsis. In some embodiments, the values of sensitivity and specificity may be adjusted depending on priorities. In other words, the specificity or sensitivity may be chosen to be a value, with the other accuracy measure adjusted to optimize the overall accuracy. The cutoff values may be calculated or selected based on other criteria. The cutoff value may be selected to prioritize ruling-out infection over ruling-in infection in an individual.

If the sepsis status indicates sepsis or a suspicion of sepsis, methods may include performing appropriate medical procedures related to an individual with sepsis. Methods may include treating sepsis, including, for example, prescribing and administering antibiotics. The treatment for sepsis may be prophylactic. The method along with treatment may decrease the individual's risk of death compared to conventional methods of diagnosing and treating sepsis. Methods may include treating an individual with sepsis or suspected sepsis with supportive care and/or symptom management, potentially in anticipation of developing sepsis symptoms. The individual may not show definitive symptoms of sepsis, but the treatment may be prescribed to prevent or mitigate the onset of sepsis.

Methods may also include additional testing to diagnose sepsis. Additional testing may include culture analysis from a biological sample of the individual. If the sepsis status indicates sepsis, the reporting process for the measurement results may be modified. For example, whereas a routine blood test with results that do not indicate sepsis might be automatically transmitted to a laboratory information system, health information system, or the like after the results are released by the laboratory, a blood test with a sepsis indication might be held and/or flagged for review by the analysis operator, e.g., with instructions to call the physician, hand-deliver results, initiate additional testing if there is adequate sample remaining (such as biomarker testing or microbiology cultures), or otherwise take some proactive step in addition to or instead of merely releasing the results.

Embodiments may include evaluating that sepsis is not present even when the individual has systemic inflammatory response syndrome (SIRS). In other words, embodiments may be able to distinguish between when an individual has SIRS only or when the individual has sepsis (a combination of inflammation and infection). In some embodiments, methods may be able to distinguish between sepsis and other types of infection (e.g., non-systemic, localized infections). For example, certain MDW values (e.g., those between 19.0 and 19.5 units) have a higher sensitivity for predicting sepsis from SIRS, but have a lower specificity. The impact on sensitivity and specificity for early detection of sepsis from SIRS at different MDW cutoff values is provided in the below Table 1.

TABLE 1

Sensitivity and Specificity at Various MDW Cutoffs to Differentiate between SIRS and Sepsis

| Cut-off | Sensi-tivity | 95% Confidence Intervals | | Speci-ficity | 95% Confidence Intervals | |
| --- | --- | --- | --- | --- | --- | --- |
| | | Lower | Upper | | Lower | Upper |
| 19.0 | 0.821 | 0.779 | 0.856 | 0.517 | 0.470 | 0.563 |
| 19.5 | 0.784 | 0.741 | 0.823 | 0.601 | 0.555 | 0.646 |
| 20.0 | 0.740 | 0.694 | 0.782 | 0.658 | 0.612 | 0.700 |
| 20.5 | 0.683 | 0.635 | 0.728 | 0.719 | 0.675 | 0.759 |

Embodiments may also include assigning a sepsis indication to the blood sample based on evaluating the sepsis status. For example, the sepsis indication may include a label of not septic, septic, needing treatment, not needing treatment, or undetermined. The sepsis indication may also include a degree of certainty based on the comparisons. For example, the sepsis indication may include possibly septic, likely septic, or almost certainly septic. A standard deviation of monocyte volume or white blood cell count that far exceeds the applicable cutoff values may be associated with a higher degree of certainty.

Embodiments may include outputting the sepsis status. For example, the sepsis status may be outputted on a display of a computer, a mobile device, a smart watch, a terminal, a laboratory information system, a health information system, an electronic medical record, or other digital devices. In some embodiments, the sepsis status may be outputted into a physical form, such as paper.

Methods may be performed on a plurality of blood samples from one or more individuals. Aspects of the methods are described in additional detail below, including with FIGS. 5, 7A, and 8.

II. EXAMPLE SYSTEMS

Embodiments may include an automated system for evaluating a sepsis status associated with a blood sample obtained from an individual. The system may include a first module that includes an electrode assembly configured to measure direct current (DC) impedance of cells of the blood sample passing individually through a cell interrogation zone. Testing of the sample at the first module may take less than a minute.

The system may also include a data processing module in connectivity with the first module. The data processing module may include a processor and a tangible non-transitory computer readable medium. The tangible non-transitory computer readable medium may be programmed with a computer application that, when executed by the processor, causes the processor to determine a standard deviation of monocyte volume associated with the blood sample using the DC impedance of cells measured in the first module. The processor may further be caused to determine a value of a parameter associated with the blood sample using the DC impedance of cells measured in the first module. The parameter may indicate a likelihood of a white blood cell in the blood sample having a blast proliferation that is statistically different from an expected distribution of white blood cells. The processor may further be caused to compare the value of the parameter to a first cutoff value to provide a first comparison. The processor may also be caused to determine a second cutoff value based on the first comparison. In addition, the processor may be caused to compare the standard deviation of monocyte volume to the second cutoff value to provide a second comparison. Furthermore, the processor may be caused to evaluate the sepsis status associated with the blood sample based on the second comparison. The first comparison and the second comparison may be any associated comparison described herein.

The sepsis status may have a sensitivity for sepsis greater than 0.70 and a specificity for the infection greater than 0.70. The specificity and sensitivity may be any specificity and sensitivity described herein.

The system may further include a second module. If provided, the second module may be configured to determine a white blood cell count (WBC) of the blood sample. It should be understood that, in some examples, the first and second modules may be the same module. The data processing module may be in connectivity with the second module. The computer application, when executed by the processor, may cause the processor to determine the WBC associated with the blood sample. The processor may further be caused to compare the WBC to a third cutoff value to provide a third comparison. The processor may also be caused to evaluate the sepsis status associated with the blood sample based on the second comparison and the third comparison. The third comparison may be any comparison for white blood cell count described herein. The evaluation of the sepsis status may be according to any method described herein.

The computer application, when executed by the processor, may cause the processor to perform any method described herein. Aspects of the system are described in additional detail below.

III. ANALYSIS TECHNIQUES AND SYSTEMS

Figure 1B:
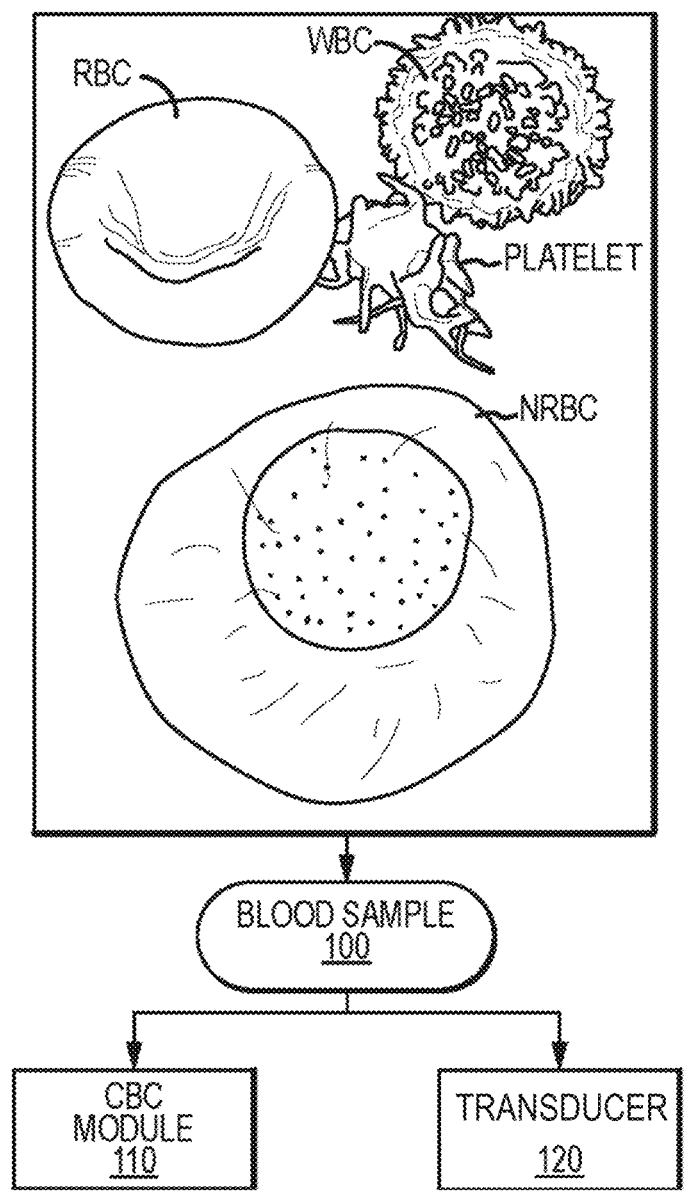
FIG. 1B illustrates aspects of blood cell analysis, according to embodiments of the present invention.

FIG. 1B illustrates aspects of an example analysis technique. As shown here, and as discussed elsewhere herein, a whole blood sample 100 may include cells such as platelets, white blood cells (WBCs), and red blood cells (RBCs), including nucleated red blood cells (NRBCs). Various RBC, WBC, and NRBC parameters, obtained from channel processing mechanisms such as a CBC module 110 or transducer 120, can be evaluated to assess the infection status of an individual. The transducer may obtain current data for blood samples as the sample passes through an aperture. The aperture may be part of a flow cell.

Figure 2:
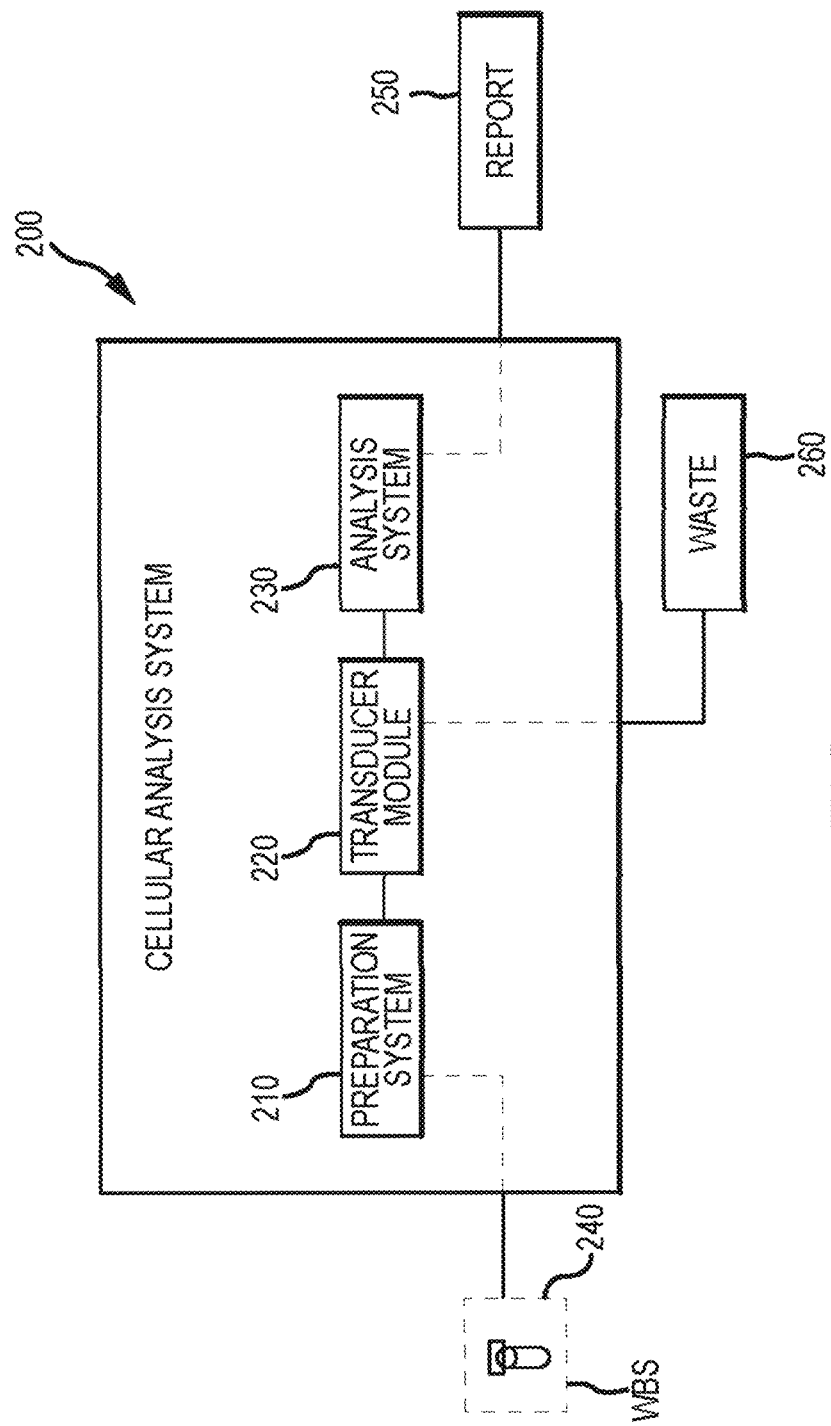
FIG. 2 schematically depicts aspects of a cellular analysis system, according to embodiments of the present invention.

FIG. 2 schematically depicts a cellular analysis system 200. As shown here, system 200 includes a preparation system 210, a transducer module 220, and an analysis system 230. While system 200 is herein described at a very high level, with reference to the three core system blocks (210, 220, and 230), system 200 includes many other system components such as central control processor(s), display system(s), fluidic system(s), temperature control system(s), user-safety control system(s), and the like. In operation, a whole blood sample (WBS) 240 can be presented to the system 200 for analysis. In some instances, WBS 240 is aspirated into system 200 with suitable aspiration techniques. After aspiration, WBS 240 can be delivered to a preparation system 210. Preparation system 210 receives WBS 240 and can perform operations involved with preparing WBS 240 for further measurement and analysis. For example, preparation system 210 may separate WBS 240 into predefined aliquots for presentation to transducer module 220. Preparation system 210 may also include mixing chambers so that appropriate reagents may be added to the aliquots. For example, where an aliquot is to be tested for differentiation of white blood cell subset populations, a lysing reagent (e.g. ERYTHROLYSE, a red blood cell lysing buffer) may be added to the aliquot to break up and remove the RBCs. Preparation system 210 may also include temperature control components to control the temperature of the reagents and/or mixing chambers. Appropriate temperature controls can improve the consistency of the operations of preparation system 210.

In some instances, predefined aliquots can be transferred from preparation system 210 to transducer module 220. As described in further detail below, transducer module 220 can perform direct current (DC) impedance, radiofrequency (RF) conductivity, light transmission, and/or light scatter measurements of cells from the WBS passing individually therethrough. Measured DC impedance, RF conductivity, and light propagation (e.g. light transmission, light scatter) parameters can be provided or transmitted to analysis system 230 for data processing. In some instances, analysis system 230 may include computer processing features and/or one or more modules or components such as those described herein with reference to the system depicted in FIG. 6 and described further below, which can evaluate the measured parameters, identify and enumerate the WBS constituents, and correlate a subset of data characterizing elements of the WBS with an infection status. As shown here, cellular analysis system 200 may generate or output a report 250 containing the evaluated infection status and/or a prescribed treatment regimen for the individual. In some instances, excess biological sample from transducer module 220 can be directed to an external (or alternatively internal) waste system 260.

Figure 3:
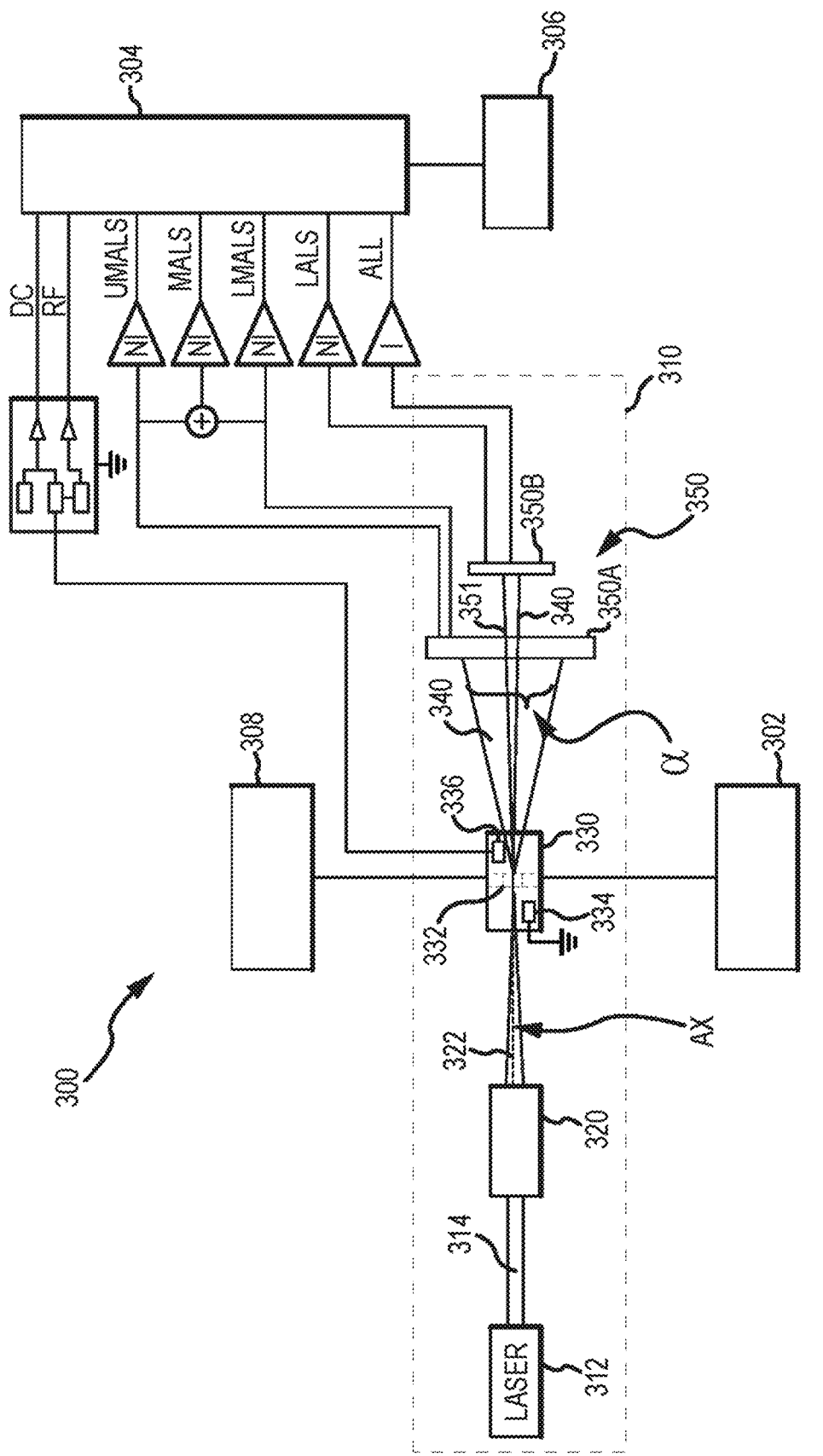
FIG. 3 provides a system block diagram illustrating aspects of a cellular analysis system according to embodiments of the present invention.

FIG. 3 illustrates in more detail a transducer module and associated components in more detail. As shown here, system 300 includes a transducer module 310 having a light or irradiation source such as a laser 312 emitting a beam 314. The laser 312 can be, for example, a 635 nm, 5 mW, solid-state laser. In some instances, system 300 may include a focus-alignment system 320 that adjusts beam 314 such that a resulting beam 322 is focused and positioned at a cell interrogation zone 332 of a flow cell 330. In some instances, flow cell 330 receives a sample aliquot from a preparation system 302. As described elsewhere herein, various fluidic mechanisms and techniques can be employed for hydrodynamic focusing of the sample aliquot within flow cell 330.

In some instances, the aliquot generally flows through the cell interrogation zone 332 such that its constituents pass through the cell interrogation zone 332 one at a time. In some cases, a system 300 may include a cell interrogation zone or other feature of a transducer module or blood analysis instrument such as those described in U.S. Pat. Nos. 5,125,737; 6,228,652; 7,390,662; 8,094,299; and 8,189,187, the contents of which are incorporated herein by references. For example, a cell interrogation zone 332 may be defined by a square transverse cross-section measuring approximately 50×50 microns, and having a length (measured in the direction of flow) of approximately 65 microns. Flow cell 330 may include an electrode assembly having first and second electrodes 334, 336 for performing DC impedance and RF conductivity measurements of the cells passing through cell interrogation zone 332. Signals from electrodes 334, 336 can be transmitted to analysis system 304. The electrode assembly can analyze volume and conductivity characteristics of the cells using low-frequency current and high-frequency current, respectively. For example, low-frequency DC impedance measurements can be used to analyze the volume of each individual cell passing through the cell interrogation zone. Relatedly, high-frequency RF current measurements can be used to determine the conductivity of cells passing through the cell interrogation zone. Because cell walls act as conductors to high frequency current, the high frequency current can be used to detect differences in the insulating properties of the cell components, as the current passes through the cell walls and through each cell interior. High frequency current can be used to characterize nuclear and granular constituents and the chemical composition of the cell interior.

Incoming beam 322 travels along beam axis AX and irradiates the cells passing through cell interrogation zone 332, resulting in light propagation within an angular range a (e.g. scatter, transmission) emanating from the zone 332. Exemplary systems are equipped with sensor assemblies that can detect light within three, four, five, or more angular ranges within the angular range a, including light associated with an extinction or axial light loss measure as described elsewhere herein. As shown here, light propagation 340 can be detected by a light detection assembly 350, optionally having a light scatter detector unit 350A and a light scatter and transmission detector unit 350B. In some instances, light scatter detector unit 350A includes a photoactive region or sensor zone for detecting and measuring upper median angle light scatter (UMALS), for example light that is scattered or otherwise propagated at angles relative to a light beam axis within a range from about 20 to about 42 degrees. In some instances, UMALS corresponds to light propagated within an angular range from between about 20 to about 43 degrees, relative to the incoming beam axis which irradiates cells flowing through the interrogation zone. Light scatter detector unit 350A may also include a photoactive region or sensor zone for detecting and measuring lower median angle light scatter (LMALS), for example light that is scattered or otherwise propagated at angles relative to a light beam axis within a range from about 10 to about 20 degrees. In some instances, LMALS corresponds to light propagated within an angular range from between about 9 to about 19 degrees, relative to the incoming beam axis which irradiates cells flowing through the interrogation zone.

A combination of UMALS and LMALS is defined as median angle light scatter (MALS), which is light scatter or propagation at angles between about 9 degrees and about 43 degrees relative to the incoming beam axis which irradiates cells flowing through the interrogation zone.

As shown in FIG. 3, the light scatter detector unit 350A may include an opening 351 that allows low angle light scatter or propagation 340 to pass beyond light scatter detector unit 350A and thereby reach and be detected by light scatter and transmission detector unit 350B. According to some embodiments, light scatter and transmission detector unit 350B may include a photoactive region or sensor zone for detecting and measuring lower angle light scatter (LALS), for example light that is scattered or propagated at angles relative to an irradiating light beam axis of about 5.1 degrees. In some instances, LALS corresponds to light propagated at an angle of less than about 9 degrees, relative to the incoming beam axis which irradiates cells flowing through the interrogation zone. In some instances, LALS corresponds to light propagated at an angle of less than about 10 degrees, relative to the incoming beam axis which irradiates cells flowing through the interrogation zone. In some instances, LALS corresponds to light propagated at an angle of about 1.9 degrees±0.5 degrees, relative to the incoming beam axis which irradiates cells flowing through the interrogation zone. In some instances, LALS corresponds to light propagated at an angle of about 3.0 degrees±0.5 degrees, relative to the incoming beam axis which irradiates cells flowing through the interrogation zone. In some instances, LALS corresponds to light propagated at an angle of about 3.7 degrees±0.5 degrees, relative to the incoming beam axis which irradiates cells flowing through the interrogation zone. In some instances, LALS corresponds to light propagated at an angle of about 5.1 degrees±0.5 degrees, relative to the incoming beam axis which irradiates cells flowing through the interrogation zone. In some instances, LALS corresponds to light propagated at an angle of about 7.0 degrees±0.5 degrees, relative to the incoming beam axis which irradiates cells flowing through the interrogation zone.

According to some embodiments, light scatter and transmission detector unit 350B may include a photoactive region or sensor zone for detecting and measuring light transmitted axially through the cells, or propagated from the irradiated cells, at an angle of 0 degrees relative to the incoming light beam axis. In some cases, the photoactive region or sensor zone may detect and measure light propagated axially from cells at angles of less than about 1 degree relative to the incoming light beam axis. In some cases, the photoactive region or sensor zone may detect and measure light propagated axially from cells at angles of less than about 0.5 degrees relative to the incoming light beam axis less. Such axially transmitted or propagated light measurements correspond to axial light loss (ALL or AL2). As noted in previously incorporated U.S. Pat. No. 7,390,662, when light interacts with a particle, some of the incident light changes direction through the scattering process (i.e. light scatter) and part of the light is absorbed by the particles. Both of these processes remove energy from the incident beam. When viewed along the incident axis of the beam, the light loss can be referred to as forward extinction or axial light loss. Additional aspects of axial light loss measurement techniques are described in U.S. Pat. No. 7,390,662 at column 5, line 58 to column 6, line 4.

As such, the cellular analysis system 300 provides means for obtaining light propagation measurements, including light scatter and/or light transmission, for light emanating from the irradiated cells of the biological sample at any of a variety of angles or within any of a variety of angular ranges, including ALL and multiple distinct light scatter or propagation angles. For example, light detection assembly 350, including appropriate circuitry and/or processing units, provides a means for detecting and measuring UMALS, LMALS, LALS, MALS, and ALL.

Wires or other transmission or connectivity mechanisms can transmit signals from the electrode assembly (e.g. electrodes 334, 336), light scatter detector unit 350A, and/or light scatter and transmission detector unit 350B to analysis system 304 for processing. For example, measured DC impedance, RF conductivity, light transmission, and/or light scatter parameters can be provided or transmitted to analysis system 304 for data processing. In some instances, analysis system 304 may include computer processing features and/or one or more modules or components such as those described herein with reference to the system depicted in FIG. 6, which can evaluate the measured parameters, identify and enumerate biological sample constituents, and correlate a subset of data characterizing elements of the biological sample with an infection status of the individual. As shown here, cellular analysis system 300 may generate or output a report 306 containing the evaluated infection status and/or a prescribed treatment regimen for the individual. In some instances, excess biological sample from transducer module 310 can be directed to an external (or alternatively internal) waste system 308. In some instances, a cellular analysis system 300 may include one or more features of a transducer module or blood analysis instrument such as those described in previously incorporated U.S. Pat. Nos. 5,125,737; 6,228,652; 8,094,299; and 8,189,187.

Figure 4:
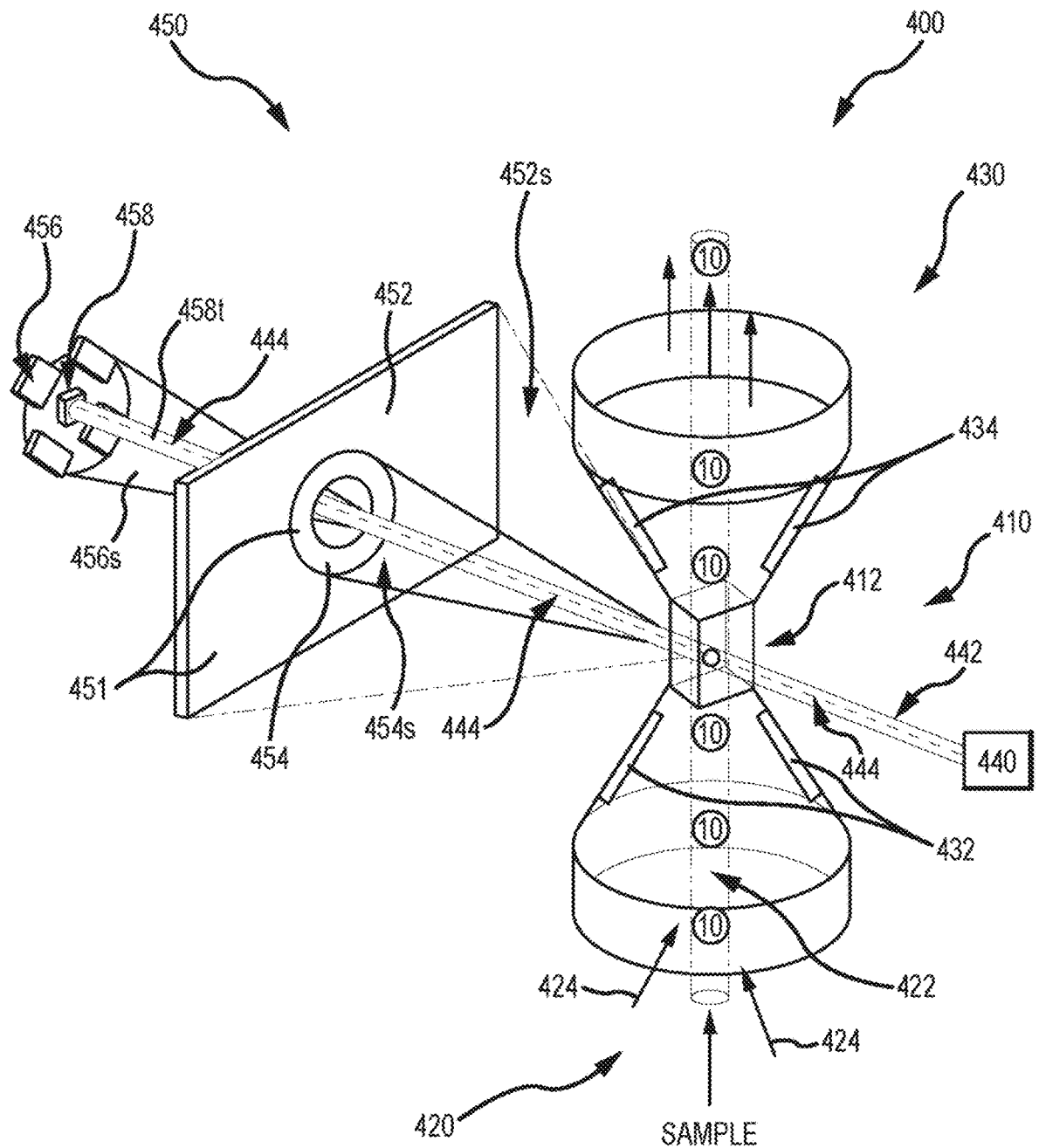
FIG. 4 illustrates aspects of an automated cellular analysis system for assessing a likelihood of infection in an individual, according to embodiments of the present invention.

FIG. 4 illustrates aspects of an automated cellular analysis system for evaluating the infection status in an individual, according to embodiments of the present invention. In particular, the infection status can be evaluated based on a biological sample obtained from blood of the individual. As shown here, an analysis system or transducer 400 may include an optical element 410 having a cell interrogation zone 412. The transducer also provides a flow path 420, which delivers a hydrodynamically focused stream 422 of a biological sample toward the cell interrogation zone 412. For example, as the sample stream 422 is projected toward the cell interrogation zone 412, a volume of sheath fluid 424 can also enter the optical element 410 under pressure, so as to uniformly surround the sample stream 422 and cause the sample stream 422 to flow through the center of the cell interrogation zone 412, thus achieving hydrodynamic focusing of the sample stream. In this way, individual cells of the biological sample, passing through the cell interrogation zone one cell at a time, can be precisely analyzed.

Transducer module or system 400 also includes an electrode assembly 430 that measures direct current (DC) impedance and radiofrequency (RF) conductivity of cells 10 of the biological sample passing individually through the cell interrogation zone 412. The electrode assembly 430 may include a first electrode mechanism 432 and a second electrode mechanism 434. As discussed elsewhere herein, low-frequency DC measurements can be used to analyze the volume of each individual cell passing through the cell interrogation zone. In some instances, the standard deviation of the volume of monocytes may be derived with low-frequency DC measurements. Relatedly, high-frequency RF current measurements can be used to determine the conductivity of cells passing through the cell interrogation zone. Such conductivity measurements can provide information regarding the internal cellular content of the cells. For example, high frequency RF current can be used to analyze nuclear and granular constituents, as well as the chemical composition of the cell interior, of individual cells passing through the cell interrogation zone.

The system 400 also includes a light source 440 oriented to direct a light beam 442 along a beam axis 444 to irradiate the cells 10 of the biological sample individually passing through the cell interrogation zone 412. Relatedly, the system 400 includes a light detection assembly 450 optically coupled with the cell interrogation zone, so as to measure light scattered by and transmitted through the irradiated cells 10 of the biological sample. The light detection assembly 450 can include a plurality of light sensor zones that detect and measure light propagating from the cell interrogation zone 412. In some instances, the light detection assembly detects light propagated from the cell interrogation zone at various angles or angular ranges relative to the irradiating beam axis. For example, light detection assembly 450 can detect and measure light that is scattered at various angles by the cells, as well as light that is transmitted axially by the cells along the beam axis. The light detection assembly 450 can include a first sensor zone 452 that measures a first scattered or propagated light 452s within a first range of angles relative to the light beam axis 444. The light detection assembly 450 can also include a second sensor zone 454 that measures a second scattered or propagated light 454s within a second range of angles relative to the light beam axis 444. As shown here, the second range of angles for scattered or propagated light 454s is different from the first range of angles for scattered or propagated light 452s. Further, the light detection assembly 450 can include a third sensor zone 456 that measures a third scattered or propagated light 456s within a third range of angles relative to the light beam axis 444. As shown here, the third range of angles for scattered or propagated light 456s is different from both the first range of angles for scattered or propagated light 452s and the second range of angles for scattered or propagated light 454s. The light detection assembly 450 also includes a fourth sensor zone 458 that measures axial light 458t transmitted through the cells of the biological sample passing individually through the cell interrogation zone 412 or propagated from the cell interrogation zone along the axis beam. In some instances, each of the sensor zones 452, 454, 456, and 458 are disposed at a separate sensor associated with that specific sensor zone. In some instances, one or more of the sensor zones 452, 454, 456, and 458 are disposed on a common sensor of the light detection assembly 450. For example, the light detection assembly may include a first sensor 451 that includes first sensor zone 452 and second sensor zone 454. Hence, a single sensor may be used for detecting or measuring two or more types (e.g. low angle, medium angle, or high angle) of light scatter or propagation.

Figure 4A:
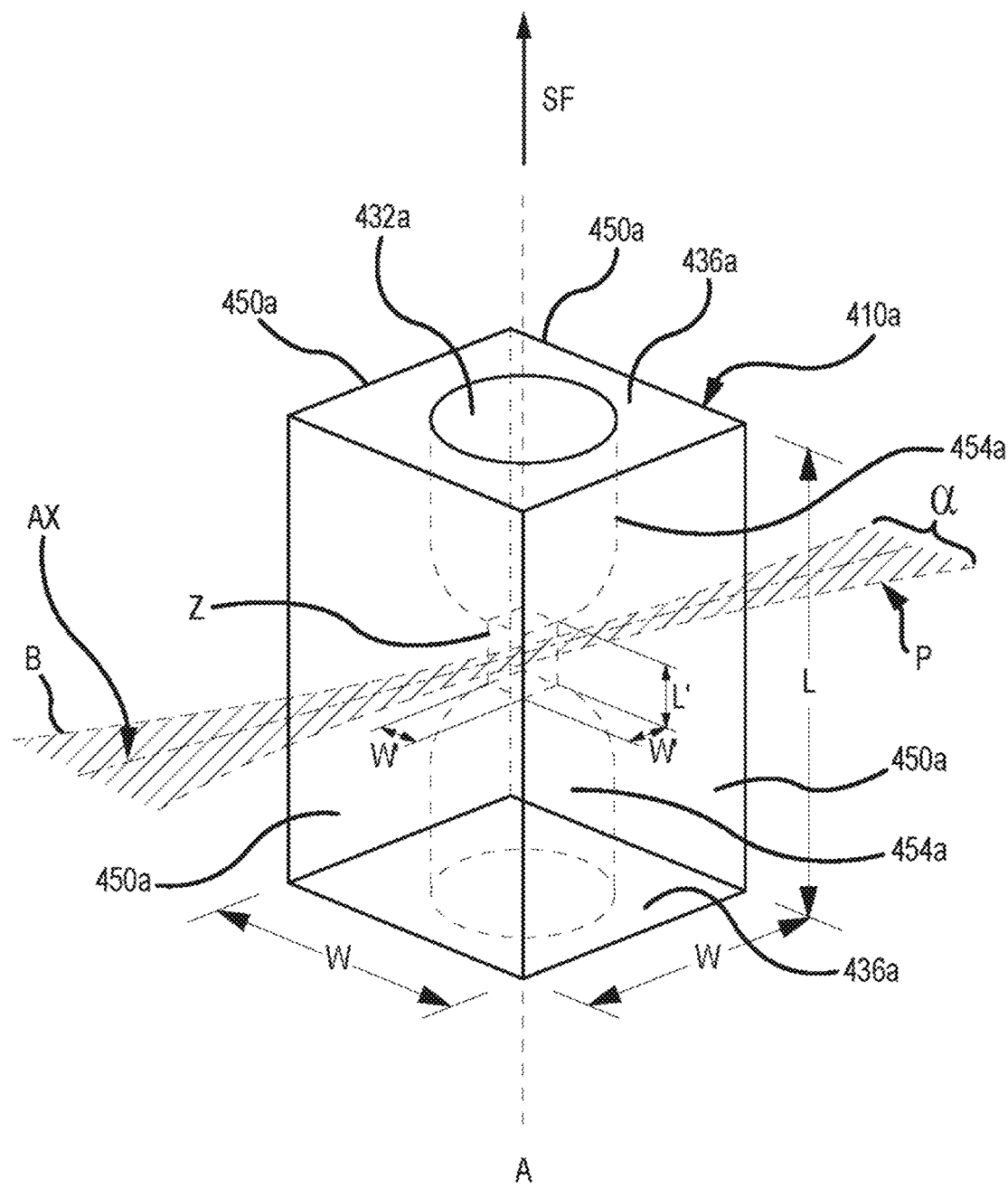
FIG. 4A shows aspects of an optical element of a cellular analysis system, according to embodiments of the present invention.

Automated cellular analysis systems may include any of a variety of optical elements or transducer features. For example, as depicted in FIG. 4A, an optical element 410a of a cellular analysis system transducer may have a square prism shape, with four rectangular, optically flat sides 450a and opposing end walls 436a. In some instances, the respective widths W of each side 450a are the same, each measuring about 4.2 mm, for example. In some instances, the respective lengths L of each side 450a are the same, each measuring about 6.3 mm, for example. In some instances, all or part of the optical element 410a may be fabricated from fused silica, or quartz. A flow passageway 432a formed through a central region of optical element 410a may be concentrically configured with respect to a longitudinal axis A passing through the center of element 410a and parallel to a direction of sample-flow as indicated by arrow SF. Flow passageway 432a includes a cell interrogation zone Z and a pair of opposing tapered bore holes 454a having openings in the vicinity of their respective bases that fluidically communicate with the cell interrogation zone. In some instances, the transverse cross-section of the cell interrogation zone Z is square in shape, the width W' of each side nominally measuring 50 microns±10 microns. In some instances, the length L' of the cell interrogation zone Z, measured along axis A, is about 1.2 to 1.4 times the width W' of the interrogation zone. For example, the length L' may be about 65 microns±10 microns. As noted elsewhere herein, DC and RF measurements can be made on cells passing through the cell interrogation zone. In some instances, the maximum diameter of the tapered bore holes 454a, measured at end walls 436a, is about 1.2 mm. An optical structure 410a of the type described can be made from a quartz square rod containing a 50×50 micron capillary opening, machined to define the communicating bore holes 454a, for example. A laser or other irradiation source can produce a beam B that is directed through or focused into the cell interrogation zone. For example, the beam may be focused into an elliptically shaped waist located within the interrogation zone Z at a location through which the cells are caused to pass. A cellular analysis system may include a light detection assembly that is configured to detect light which emanates from the optical element 410a, for example light P that is propagated from the cell interrogation zone Z which contains illuminated or irradiated cells flowing therewithin. As depicted here, light P can propagate or emanate from the cell interrogation zone Z within an angular range a, and thus can be measured or detected at selected angular positions or angular ranges relative to the beam axis AX. Relatedly, a light detection assembly can detect light scattered or axially transmitted in a forward plane within various angular ranges with respect to an axis AX of beam B. As discussed elsewhere herein, one or more light propagation measurements can be obtained for individual cells passing through the cell interrogation zone one at a time. In some cases, a cellular analysis system may include one or more features of a transducer or cell interrogation zone such as those described in U.S. Pat. Nos. 5,125,737; 6,228,652; 8,094,299; and 8,189,187, the contents of which are incorporated herein by reference.

Figure 5:
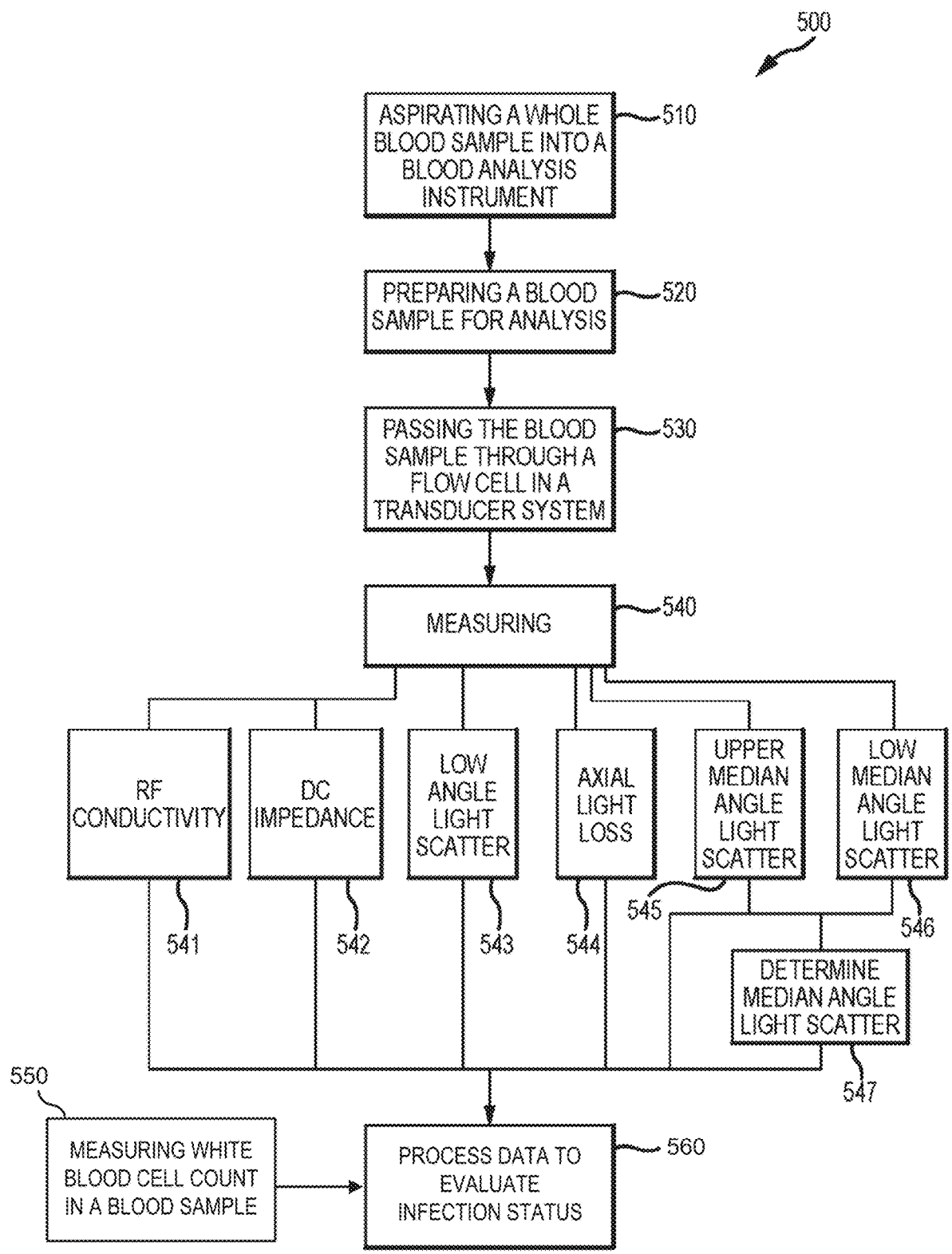
FIG. 5 depicts aspects of an exemplary method for evaluating an infection status of an individual, according to embodiments of the present invention.

FIG. 5 depicts aspects of an exemplary method 500 for evaluating an infection status (e.g., a sepsis status) associated with a blood sample obtained from an individual. Method 500 includes introducing a blood sample into a blood analysis system, as indicated by step 510. As shown in step 520, the method may also include preparing the blood sample by dividing the sample into aliquots and mixing the aliquot samples with appropriate reagents. In step 530, the samples can be passed through a flow cell in a transducer system such that sample constituents (e.g. blood cells) pass through a cell interrogation zone in a one by one fashion. The constituents can be irradiated by a light source, such as a laser. In step 540, any combination RF conductivity 541, DC impedance 542, first angular light propagation 543 (e.g. LALS), second angular light propagation 544 (e.g. AL2), third angular light propagation 545 (e.g. UMAL), and/or fourth angular light propagation 546 (e.g. LMALS) may be measured. As depicted by step 547, the third and fourth angular light propagation measurements can be used to determine a fifth angular light propagation measurement (e.g. MALS). Alternatively, MALS can be measured directly. In some examples, step 540 may include DC impedance 542 and may exclude any combination of the other measurements. In step 550, the white blood cell count in a blood sample may optionally be measured. The blood sample may be a second blood sample from the individual or may be the same blood sample that is flowed through the flow cell. As discussed elsewhere herein, certain measurements or combinations of measurements can be processed, as indicated by step 560, so as to provide a likelihood of infection. Optionally, methods may also include determining a treatment regime based on the predicted likelihood of infection.

A cellular analysis system may be configured to correlate a subset of DC impedance, RF conductivity, angular light measurements (e.g. first scattered light, second scattered light), the axial light measurements from the cells of the biological sample with an infection status, which may include sepsis status. As discussed elsewhere herein, in some instances at least a portion of the correlation can be performed using one or more software modules executable by one or more processors, one or more hardware modules, or any combination thereof. Processors or other computer or module systems may be configured to receive as an input values for the various measurements or parameters and automatically output the predicted evaluated infection status. In some instances, one or more of the software modules, processors, and/or hardware modules may be included as a component of a hematology system that is equipped to obtain multiple light angle detection parameters, such as Beckman Coulter's UniCel® DxH™ 800 or DxH™ 900 Cellular Analysis System. In some instances, one or more of the software modules, processors, and/or hardware modules may be includes as a component of a stand-alone computer that is in operative communication or connectivity with a hematology system that is equipped to obtain multiple light angle detection parameters, such as Beckman Coulter's UniCel® DxH™ 800 System or DxH™ 900 System. In some instances, at least a portion of the correlation can be performed by one or more of the software modules, processors, and/or hardware modules that receive data from a hematology system that is equipped to obtain multiple light angle detection parameters, such as Beckman Coulter's UniCel® DxH™ 800 or DxH™ 900 System remotely via the internet or any other over wired and/or wireless communication network. Relatedly, each of the devices or modules according to embodiments of the present invention can include one or more software modules on a computer readable medium that is processed by a processor, or hardware modules, or any combination thereof.

Figure 6:
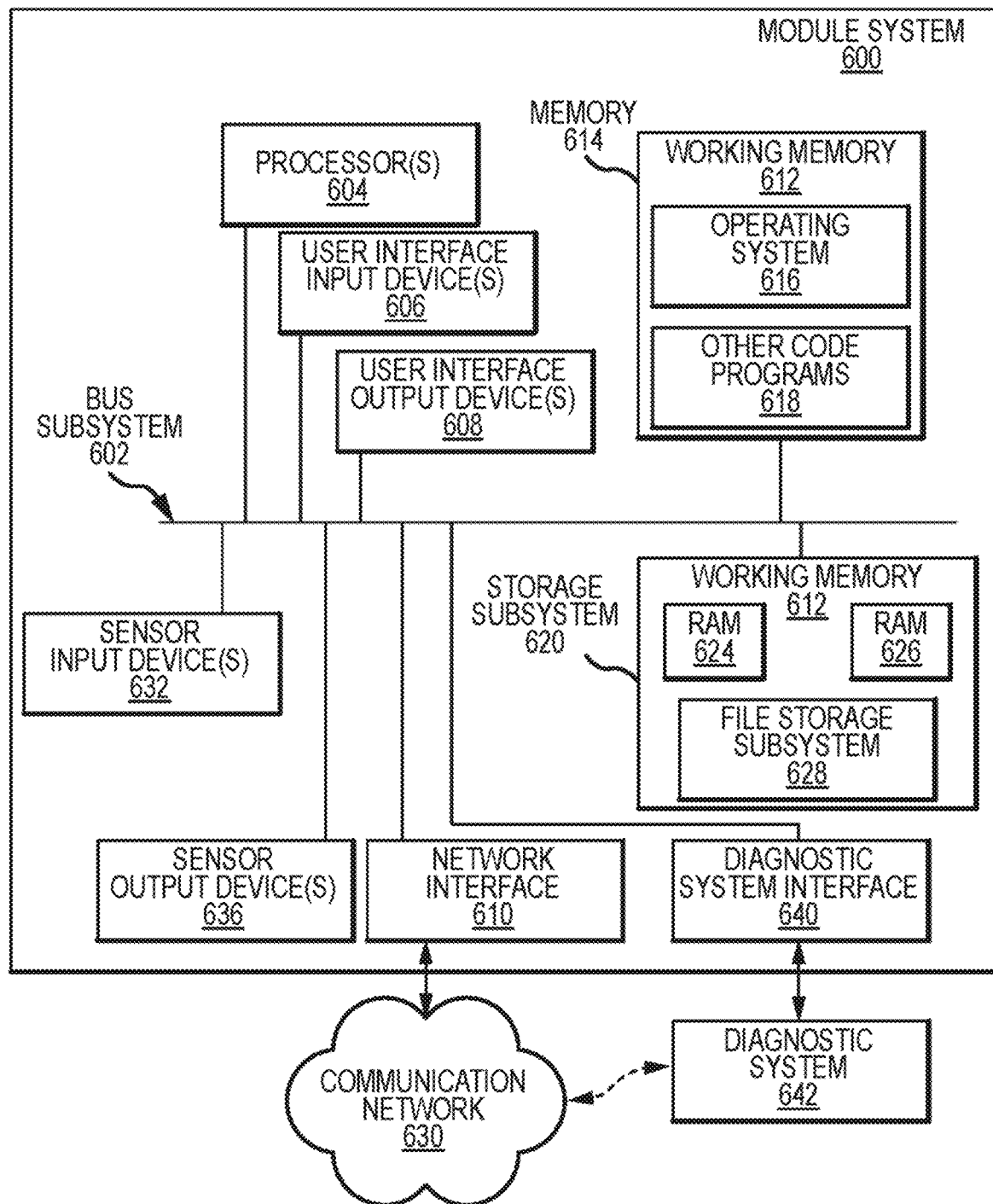
FIG. 6 provides a simplified block diagram of an exemplary module system, according to embodiments of the present invention.

FIG. 6 is a simplified block diagram of an exemplary module system that broadly illustrates how individual system elements for a module system 600 may be implemented in a separated or more integrated manner. Module system 600 may be part of or in connectivity with a cellular analysis system for evaluating the infection status according to embodiments of the present invention. Module system 600 is well suited for producing data or receiving input related to evaluate the infection status. In some instances, module system 600 includes hardware elements that are electrically coupled via a bus subsystem 602, including one or more processors 604, one or more input devices 606 such as user interface input devices, and/or one or more output devices 608 such as user interface output devices. In some instances, system 600 includes a network interface 610, and/or a diagnostic system interface 640 that can receive signals from and/or transmit signals to a diagnostic system 642. In some instances, system 600 includes software elements, for example shown here as being currently located within a working memory 612 of a memory 614, an operating system 616, and/or other code 618, such as a program configured to implement one or more aspects of the techniques disclosed herein. Each of the calculations or operations described herein may be performed using a computer or other processor having hardware, software, and/or firmware. The various method steps may be performed by modules, and the modules may comprise any of a wide variety of digital and/or analog data processing hardware and/or software arranged to perform the method steps described herein. The modules optionally comprising data processing hardware adapted to perform one or more of these steps by having appropriate machine programming code associated therewith, the modules for two or more steps (or portions of two or more steps) being integrated into a single processor board or separated into different processor boards in any of a wide variety of integrated and/or distributed processing architectures. These methods and systems will often employ a tangible media embodying machine-readable code with instructions for performing any one or more of the method or process steps described herein.

In some embodiments, module system 600 may include a storage subsystem 620 that can store the basic programming and data constructs that provide the functionality of the various techniques disclosed herein. For example, software modules implementing the functionality of method aspects, as described herein, may be stored in storage subsystem 620. These software modules may be executed by the one or more processors 604. In a distributed environment, the software modules may be stored on a plurality of computer systems and executed by processors of the plurality of computer systems. Storage subsystem 620 can include memory subsystem 622 and file storage subsystem 628. Memory subsystem 622 may include a number of memories including a main random access memory (RAM) 626 for storage of instructions and data during program execution and a read only memory (ROM) 624 in which fixed instructions are stored. File storage subsystem 628 can provide persistent (non-volatile) storage for program and data files, and may include tangible storage media which may optionally embody patient, treatment, assessment, or other data. File storage subsystem 628 may include a hard disk drive, a floppy disk drive along with associated removable media, a Compact Digital Read Only Memory (CD-ROM) drive, an optical drive, DVD, CD-R, CD RW, solid-state removable memory, other removable media cartridges or disks, and the like. One or more of the drives may be located at remote locations on other connected computers at other sites coupled to module system 600. In some instances, systems may include a computer-readable storage medium or other tangible storage medium that stores one or more sequences of instructions which, when executed by one or more processors, can cause the one or more processors to perform any aspect of the techniques or methods disclosed herein. One or more modules implementing the functionality of the techniques disclosed herein may be stored by file storage subsystem 628. In some embodiments, the software or code will provide protocol to allow the module system 600 to communicate with communication network 630. Optionally, such communications may include dial-up or internet connection communications.

It is appreciated that system 600 can be configured to carry out various aspects of methods of the present invention. In this manner, system 600 is a specialized system. For example, processor component or module 604 can be a microprocessor control module configured to receive cellular parameter signals from a sensor input device or module 632, from a user interface input device or module 606, and/or from a diagnostic system 642, optionally via a diagnostic system interface 640 and/or a network interface 610 and a communication network 630. In some instances, sensor input device(s) may include or be part of a cellular analysis system that is equipped to obtain multiple light angle detection parameters, such as Beckman Coulter's UniCel® DxH™ 800 and/or DxH™ 900 Cellular Analysis System. In some instances, user interface input device(s) 606 and/or network interface 610 may be configured to receive cellular parameter signals generated by a cellular analysis system that is equipped to obtain multiple light angle detection parameters, such as Beckman Coulter's UniCel® DxH™ 800 and/or DxH™ 900 Cellular Analysis System. In some instances, diagnostic system 642 may include or be part of a cellular analysis system that is equipped to obtain multiple light angle detection parameters, such as Beckman Coulter's UniCel® DxH™ 800 and/or DxH™ 900 Cellular Analysis System.

Processor component or module 604 can also be configured to transmit cellular parameter signals, optionally processed according to any of the techniques disclosed herein, to sensor output device or module 636, to user interface output device or module 608, to network interface device or module 610, to diagnostic system interface 640, or any combination thereof. Each of the devices or modules according to embodiments of the present invention can include one or more software modules on a computer readable medium that is processed by a processor, or hardware modules, or any combination thereof. Any of a variety of commonly used platforms, such as Windows, Mac, and Unix, along with any of a variety of programming languages, may be used to implement embodiments of the present invention.

User interface input devices 606 may include, for example, a touchpad, a keyboard, pointing devices such as a mouse, a trackball, a graphics tablet, a scanner, a joystick, a touchscreen incorporated into a display, audio input devices such as voice recognition systems, microphones, and other types of input devices. User input devices 606 may also download a computer executable code from a tangible storage media or from communication network 630, the code embodying any of the methods or aspects thereof disclosed herein. It will be appreciated that terminal software may be updated from time to time and downloaded to the terminal as appropriate. In general, use of the term "input device" is intended to include a variety of conventional and proprietary devices and ways to input information into module system 600.

User interface output devices 606 may include, for example, a display subsystem, a printer, a fax machine, or non-visual displays such as audio output devices. The display subsystem may be a cathode ray tube (CRT), a flat-panel device such as a liquid crystal display (LCD), a light-emitting diode (LED) display, an organic light-emitting diode (OLED) display, a plasma display, a projection device, or the like. The display subsystem may also provide a non-visual display such as via audio output devices. In general, use of the term "output device" is intended to include a variety of conventional and proprietary devices and ways to output information from module system 600 to a user. The results of any method or operation described herein (e.g. an infection status) may be displayed on an output device.

Bus subsystem 602 provides a mechanism for letting the various components and subsystems of module system 600 communicate with each other as intended or desired. The various subsystems and components of module system 600 need not be at the same physical location but may be distributed at various locations within a distributed network. Although bus subsystem 602 is shown schematically as a single bus, alternate embodiments of the bus subsystem may utilize multiple busses.

Network interface 610 can provide an interface to an outside network 630 or other devices. Outside communication network 630 can be configured to effect communications as needed or desired with other parties. It can thus receive an electronic packet from module system 600 and transmit any information as needed or desired back to module system 600. As depicted here, communication network 630 and/or diagnostic system interface 642 may transmit information to or receive information from a diagnostic system 642 that is equipped to obtain multiple light angle detection parameters, such as Beckman Coulter's UniCel® DxH™ 800 or DxH™ 900 Cellular Analysis System.

In addition to providing such infrastructure communications links internal to the system, the communications network system 630 may also provide a connection to other networks such as the internet and may comprise a wired, wireless, modem, and/or other type of interfacing connection.

It will be apparent to the skilled artisan that substantial variations may be used in accordance with specific requirements. For example, customized hardware might also be used and/or particular elements might be implemented in hardware, software (including portable software, such as applets), or both. Further, connection to other computing devices such as network input/output devices may be employed. Module terminal system 600 itself can be of varying types including a computer terminal, a personal computer, a portable computer, a workstation, a network computer, or any other data processing system. Due to the ever-changing nature of computers and networks, the description of module system 600 depicted in FIG. 6 is intended only as a specific example for purposes of illustrating one or more embodiments of the present invention. Many other configurations of module system 600 are possible having more or less components than the module system depicted in FIG. 6. Any of the modules or components of module system 600, or any combinations of such modules or components, can be coupled with, or integrated into, or otherwise configured to be in connectivity with, any of the cellular analysis system embodiments disclosed herein. Relatedly, any of the hardware and software components discussed above can be integrated with or configured to interface with other medical assessment or treatment systems used at other locations.

In some embodiments, the module system 600 can be configured to receive one or more cellular analysis parameters of a patient at an input module. Cellular analysis parameter data can be transmitted to an assessment module where an infection status is evaluated, predicted, analyzed, or determined. The infection status can be output to a system user via an output module. In some cases, the module system 600 can determine an initial treatment or induction protocol for the patient, based on one or more cellular analysis parameters and/or the evaluated infection status, for example by using a treatment module. The treatment can be output to a system user via an output module. Optionally, certain aspects of the treatment can be determined by an output device, and transmitted to a treatment system or a sub-device of a treatment system. Any of a variety of data related to the patient can be input into the module system, including age, weight, sex, treatment history, medical history, and the like. Parameters of treatment regimens or diagnostic evaluations can be determined based on such data.

Relatedly, in some instances a system includes a processor configured to receive the cell population data as input. Optionally, a processor, storage medium, or both, may be incorporated within a hematology or cellular analysis machine. In some instances, the hematology machine may generate cell population data or other information for input into the processor. In some instances, a processor, a storage medium, or both, can be incorporated within a computer, and the computer can be in communication with a hematology machine. In some instances, a processor, a storage medium, or both, can be incorporated within a computer, and the computer can be in remote communication with a hematology machine via a network.

IV. CELL POPULATION DATA

In addition to a differential count, once the WBC subpopulations are formed, the mean (MN) and standard deviation (SD) values for the grades of various morphologic parameters (e.g. volume, conductivity, and angles of light scatter or propagation) can be calculated separately for leukocytes and other blood cells. For example, a WBC differential channel can provide measurement data for neutrophils, lymphocytes, monocytes, eosinophils, and/or basophils and an nRBC channel can provide measurement data for non-nucleated red blood cells or a non-nucleated red blood cell parameter, as described elsewhere herein. As a result, a vast amount of data directly correlating to blood cell morphology can be generated. This information can be called collectively "Cell Population Data" (CPD). Table 2 depicts a variety of Cell Population Data parameters which may be obtained based on a biological sample of an individual. SD-V-MO may be a parameter used in embodiments. Embodiments may exclude any subset of the parameters listed in Table 2. Embodiments may include or exclude any parameters for basophils. Additionally, embodiments may include any subset of the parameters listed in Table 2.

TABLE 2

Cell Population Data parameters

|  | Neutrophil NE (ne) | Lymphocyte LY (ly) | Monocyte MO (mo or mn) | Eosinophil EO (eo) | Non-nucleated red blood cell NNRBC (nnr or nnrbc) |
|---|---|---|---|---|---|
| Cell Conductivity (C) high freq. current | SD-C-NE MN-C-NE | SD-C-LY MN-C-LY | SD-C-MO MN-C-MO | SD-C-EO MN-C-EO | SD-C-NNRBC MN-C-NNRBC |
| Cell Volume (V) low freq. current | SD-V-NE MN-V-NE | SD-V-LY MN-V-LY | SD-V-MO MN-V-MO | SD-V-EO MN-V-EO | SD-V-NNRBC MN-V-NNRBC |
| Axial light loss or absorbed light (AL2 or ALL) | SD-AL2-NE MN-AL2-NE | SD-AL2-LY MN-AL2-LY | SD-AL2-MO MN-AL2-MO | SD-AL2-EO MN-AL2-EO | SD-AL2-NNRBC MN-AL2-NNRBC |
| Low-angle light scatter (LALS) | SD-LALS-NE MN-LALS-NE | SD-LALS-LY MN-LALS-LY | SD-LALS-MO MN-LALS-MO | SD-LALS-EO MN-LALS-EO | SD-LALS-NNRBC MN-LALS-NNRBC |
| Upper median-angle light scatter (UMALS) | SD-UMALS-NE MN-UMALS-NE | SD-UMALS-LY MN-UMALS-LY | SD-UMALS-MO MN-UMALS-MO | SD-UMALS-EO MN-UMALS-EO | SD-UMALS-NNRBC MN-UMALS-NNRBC |
| Lower median-angle light scatter (LMALS) | SD-LMALS-NE MN-LMALS-NE | SD-LMALS-LY MN-LMALS-LY | SD-LMALS-MO MN-LMALS-MO | SD-LMALS-EO MN-LMALS-EO | SD-LMALS-NNRBC MN-LMALS-NNRBC |
| Median-angle light scatter (MALS) [UMALS + LMALS] | SD-MALS-NE MN-MALS-NE | SD-MALS-LY MN-MALS-LY | SD-MALS-MO MN-MALS-MO | SD-MALS-EO MN-MALS-EO | SD-MALS-NNRBC MN-MALS-NNRBC |

Figure 7:
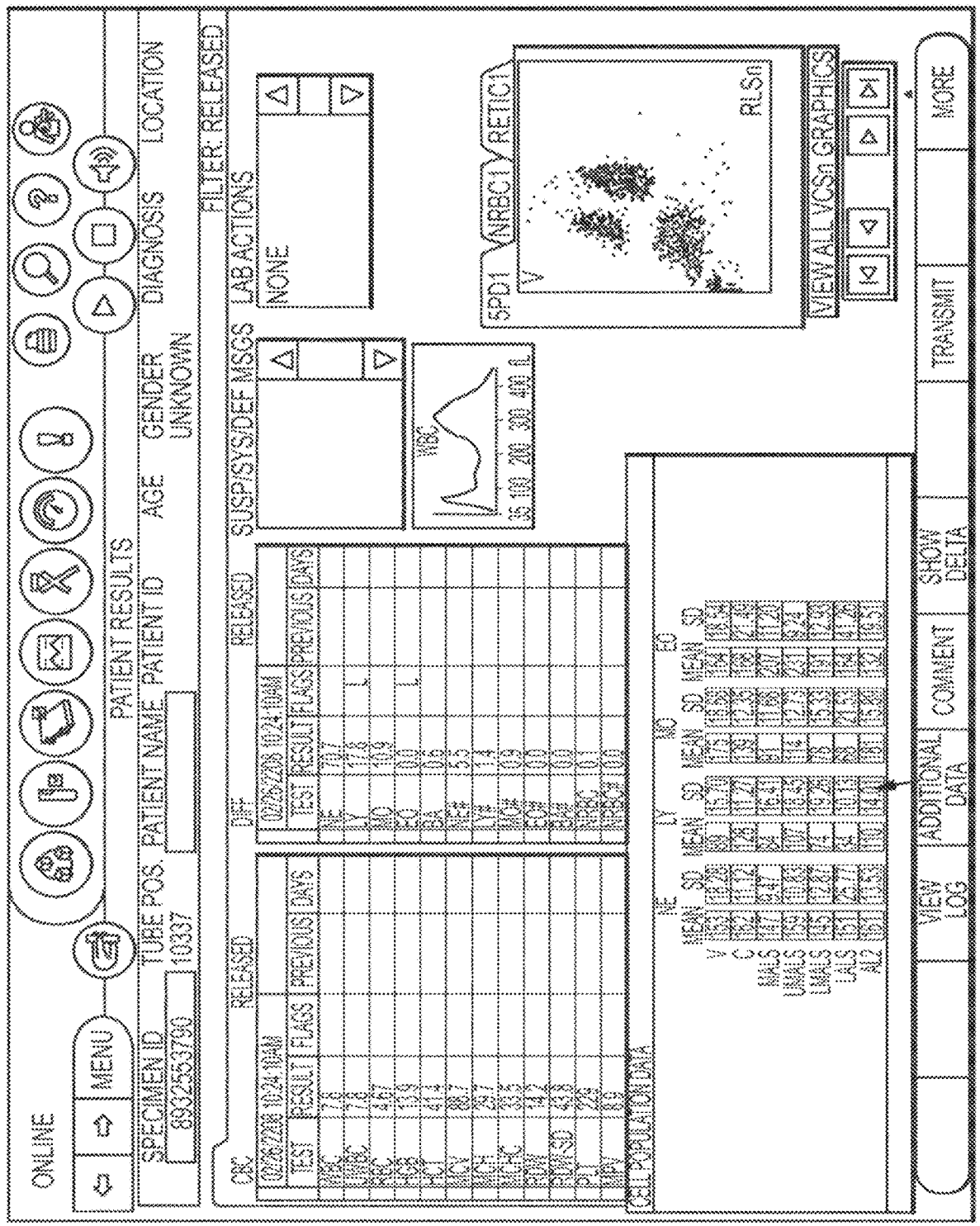
FIG. 7 depicts an example screen shot of a differential count screen, according to embodiments of the present invention.

CPD values can be viewed on the screen of an instrument, such as that depicted in FIG. 7, as well as automatically exported as an Excel file. Hence, white blood cells (WBCs) can be analyzed and individually plotted in tri-dimensional histograms, with the position of each cell on the histogram being defined by certain parameters as described herein. In some instances, systems or methods can grade the cell in a range from 1 to 256 points, for each of the parameters.

Because WBCs of the same sub-type, for example granulocytes (or neutrophils), lymphocytes, monocytes, eosinophils, and basophils, often have similar morphologic features, they may tend to be plotted in similar regions of the tri-dimensional histogram, thus forming cell populations. The number of events in each population can be used to generate a differential count. FIG. 7 depicts an exemplary screen shot of a differential count screen. As illustrated here, the WBC sub-populations are in clearly separated groups at different locations on the histogram, and are defined by different colors. The histogram shown here provides cell size (volume) in the y axis and light scatter in the x axis.

By clicking on the "Additional Data" tab, users can view the CPD values. Such CPD values can correspond to the position of the population in the histogram, and to the morphology of the WBCs under the microscope. For example, monocytes are known to be the largest of all WBCs, and have the highest mean volume. Lymphocytes are known to be the smallest of all WBCs, and have the lowest mean volume. Lymphocytes also have the lowest level of cytoplasmic granularity and the least complex nuclear morphology, and have the lowest mean light scatter, called MALS).

CPD parameters can be used to analyze cellular morphology in a quantitative, objective, and automated manner, free from the subjectivity of human interpretation, which is also very time consuming, expensive, and has limited reproducibility. CPD parameters can be used for improving the value of the CBC-diff in the diagnosis of various medical conditions that alter the morphology of WBCs.

Figure 7A:
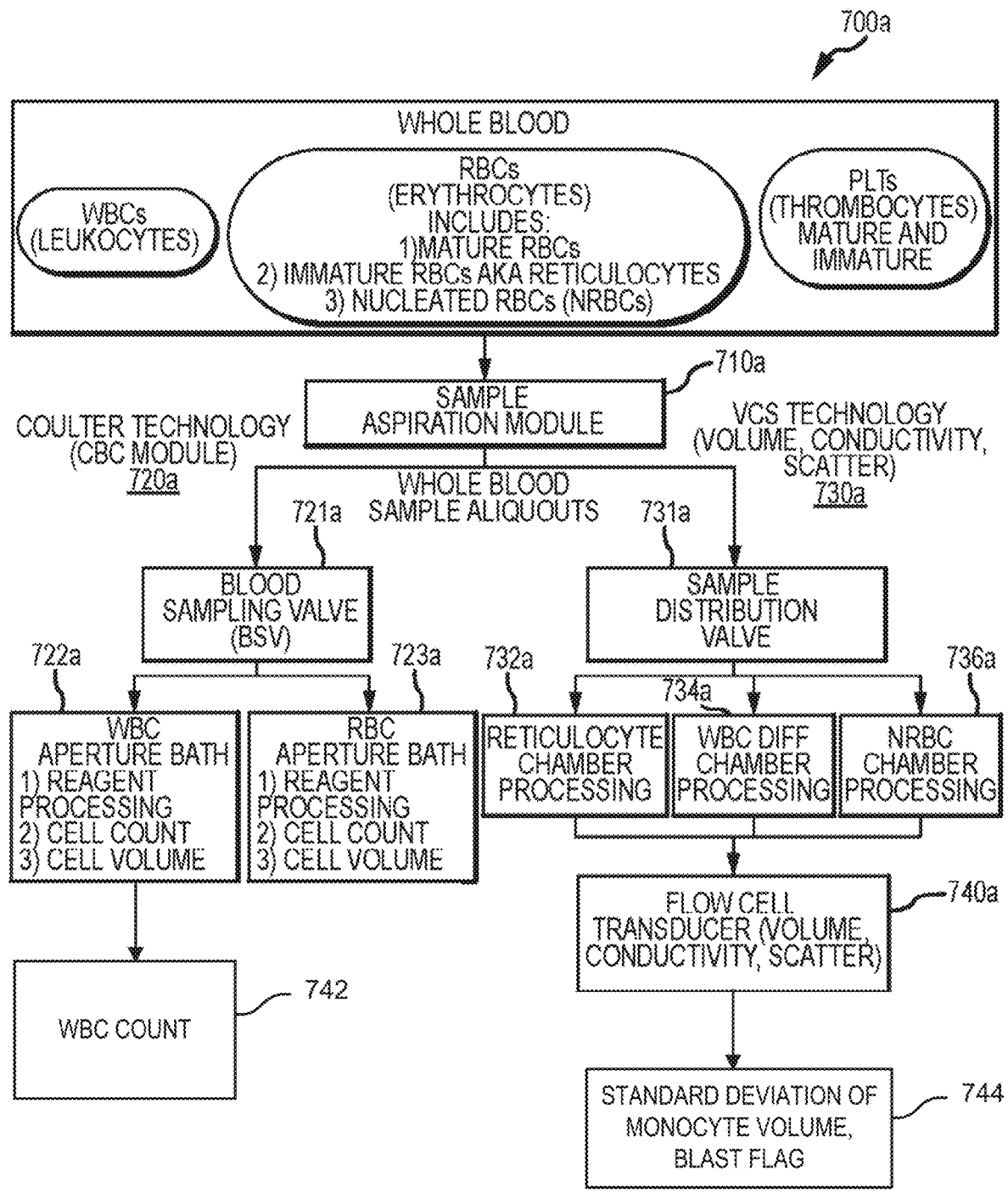
FIG. 7A schematically shows a technique for obtaining blood cell parameters, according to embodiments of the present invention.

FIG. 7A illustrates aspects of a biological sample analysis system 700a, according to embodiments of the present invention. As depicted here, infection status analysis techniques may include determining both a WBC count and a standard deviation of monocyte volume using VCS technology. Further, techniques may include determining an RBC count using an RBC aperture bath of a CBC module.

As shown here, the sample analysis system 700a includes a sample aspiration module 710a, a CBC module 720a (which incorporates Coulter technology), and a VCS module 730a (which incorporates VCS technology). The CBC module 720a includes a blood sampling valve 721a, which receives sample from aspiration module 710a. Further, the CBC module 720a includes a WBC aperture bath 722a which receives sample from BSV 721a (and can be used to determine a WBC count) and an RBC aperture bath 723a which receives sample from BSV 721a (and can be used to determine an RBC count). The VCS module 730a includes a sample distribution valve 731a, which receives sample from aspiration module 710a, and which can be used to transfer sample to a reticulocyte chamber 732a for processing with a flow cell transducer 740a. Sample distribution valve 731a can also be used to transfer sample to a WBC differential chamber 734a for processing with a flow cell transducer 740a. What is more, sample distribution valve 731a can be used to transfer sample to an NRBC chamber 736a for processing with a flow cell transducer 740a.

According to some embodiments, sample may or may not be lysed depending on where the sample is processed in the system. For example, in many instances, sample is lysed when processed using the WBC aperture bath 722a, the WBC differential chamber 734a, and the NRBC chamber 736a. In contrast, in many instances, sample is not lysed when processed using the RBC aperture bath 723a or the reticulocyte chamber 732a. Hence, as depicted in FIG. 7A, the uncorrected white blood cell count (UWBC) can be determined based on sample which is not lysed. The standard deviation of monocyte volume may be obtained from data from WBC differential chamber 734a.

According to some embodiments, a CBC module can be used to determine both a WBC count (via a WBC aperture bath) and an RBC count (via an RBC aperture bath). The parameter from the CBC module which is used in FIG. 7A is the WBC count 742. In some instances, the parameter from the CBC module may be a neutrophil count or neutrophil percentage of the WBCs. In some examples, an RBC aperture bath of a CBC module may not be required. Some embodiments may compute NE % using Beckman Coulter's UniCel DxH™ 800 or DxH™ 900 System and not use the WBC aperture bath.

As discussed herein, embodiments of the present invention encompass automated systems for evaluating an infection status in a biological sample, where the system includes a first analyzer module (e.g. implementing Coulter technology) configured to determine a white blood cell count 742 of the biological sample, a second analyzer module (e.g. implementing VCS technology) configured to determine a standard deviation of monocyte volume and a blast flag 744 of the biological sample, and a data processing module configured to evaluate the infection status based on the Coulter white blood cell count 742 and the VCS standard deviation of monocyte volume and the blast flag 744.

Figure 8:
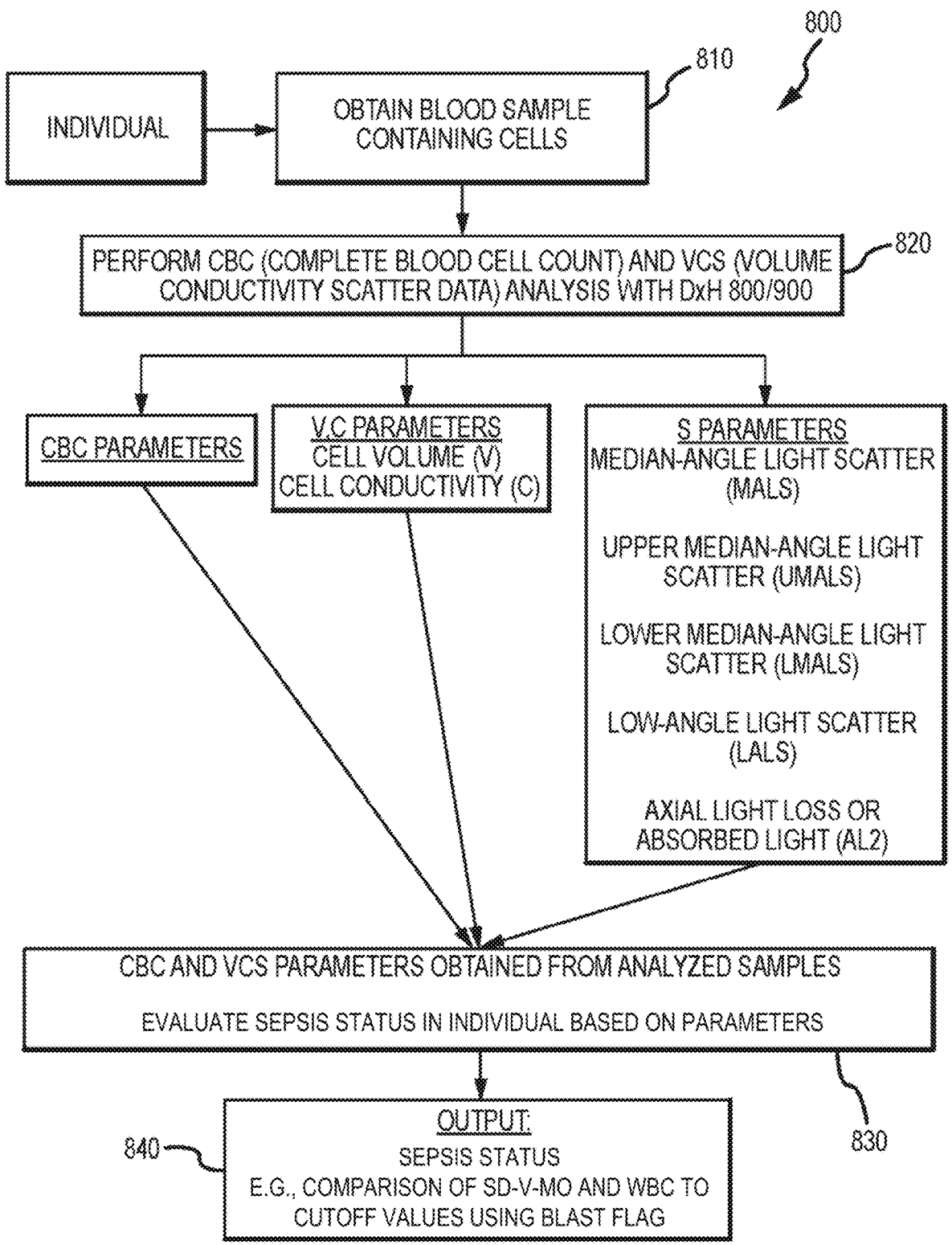
FIG. 8 illustrates aspects of a method for assessing likelihood of infection based on a biological sample obtained from an individual, according to embodiments of the present invention.

FIG. 8 schematically illustrates a method 800 for evaluating a sepsis status according to embodiments of the present invention. As depicted here, the method includes obtaining blood samples from individuals (e.g. during routine examinations), as indicated by step 810. Complete Blood Count (CBC) data, Volume Conductivity Scatter (VCS) data, or combinations thereof, can be obtained from these biological samples, using a cellular analysis system that is equipped to obtain cellular event parameters, such as Beckman Coulter's UniCel DxH™ 800 or DxH™ 900 System, as indicated by step 820. CBC parameters, VCS parameters, or combinations thereof from analyzed samples can be used to evaluate the sepsis status, as indicated by step 830. As described herein, the WBC count and the standard deviation of monocyte volume may be the only parameters or derived parameters used from the CBC and VCS parameters. Methods may also include outputting an index of the likelihood of sepsis, as indicated in step 840.

V. DIAGNOSTIC ACCURACY

Embodiments may involve different measures of diagnostic accuracy. Diagnostic accuracy involves the degree of agreement between a test and a reference method or clinical outcome measure. Diagnostic parameters of a test may not be intrinsic properties of the test and instead may depend on the clinical context of the test.

A test, compared to a reference method or clinical outcome measure, may have different outcomes: true positive, false positive, false negative, and true negative. Table 3 illustrates the relationship.

TABLE 3

Outcomes of a test result compared to a reference method.

| | Reference Standard or Clinical Outcome Measure | | |
|---|---|---|---|
| | Disease present (Sepsis) | Disease absent (Non-Sepsis) | Total |
| Test positive | True positive (TP) | False positive (FP) | TP + FP |
| Test negative | False negative (FN) | True negative (TN) | TN + FN |
| Total | TP + FN | TN + FP | Total |

Sensitivity, or sometimes called "positivity in disease," refers to the proportion of subjects who have the target condition (reference standard or clinical outcome measure shows that the disease is present) and give "test positive" results. As a formula, sensitivity can be expressed as the following:

$$\text{Sensitivity} = \frac{TP}{TP + FN}$$

Specificity, or sometimes called "negativity in health," refers to the proportion of subjects without the target condition (reference standard or clinical outcome measure shows that the disease is absent) and give "test negative" results. As a formula, specificity can be expressed as the following:

$$\text{Specificity} = \frac{TN}{TN + FP}$$

Positive predictive value (PPV) refers to the proportion of positive results that are true positives. In other words, PPV may indicate a proportion that actually have the target condition. As a formula, PPV can be expressed as the following:

$$PPV = \frac{TP}{TP + FP}$$

Negative predictive value (NPV) refers to the proportion of negative results that are true negatives. Put simply, NPV may indicate a fraction that do not have the target condition. As a formula, NPV can be expressed as the following:

$$NPV = \frac{TN}{TN + FN}$$

Predictive values may vary depending upon the prevalence of the target condition in the population being studied, although sensitivity and specificity remain the same.

A cutoff point may be created to condition the values of sensitivity and specificity of the test. An ROC curve may be a way to graphically display true positives versus false positives across a range of cutoffs and may aid in selecting a desired cutoff to achieve a clinical utility of the test. Examples of ROC curves are shown in FIG. 10, FIG. 11, FIG. 12, and FIG. 13, which will be discussed in detail in the examples below. An ROC curve may help determine cutoffs in determining the presence or absence of a target condition. The y-axis indicates the sensitivity of a test, and the x-axis indicates 1—specificity of the test. The area under curve (AUC) for an ROC curve may be used to compare test performance. The AUC may quantify the overall ability of the test to discriminate between individuals with the target condition and those without the target condition. A perfect test results in a curve that extended to the (0,1) point with an AUC of 1. A worthless test has an AUC of 0.5, indicating that the test may be no better than randomly determining whether an individual has the target condition. A line of y=x is shown in the graph to illustrate an AUC of 0.5.

Often, the distribution of test results indicating the presence of a target condition may overlap with the test results indicating the absence of the target condition. A cutoff may be set high so that the test may be unlikely to diagnose the target condition in someone who does not have the target condition (i.e., low false positive, high specificity). However, with a high cutoff, the test may be more likely to misdiagnose a person who has the target condition as someone who does not have the target condition (i.e., high false negative, low sensitivity). On the ROC curve, the choice of a high cutoff may be represented by a point near the origin.

If the cutoff is set too low, the test may diagnose correctly all or almost all the people with the target condition (i.e., high true positive, high sensitivity). However, a low cutoff may result in diagnosing the target condition in more people who do not have the target condition (i.e., high false positive, low specificity). On the ROC curve, the choice of low cutoff may be represented by a point near (1,1).

VI. EXAMPLES

A. Blood Sample Data

A blinded, prospective, observational, multicenter cohort study was conducted at three sites comprised of both academic and community hospital emergency departments in the United States. The study enrolled a total of 2,158 consecutive adult emergency-department patients (18 to 89 years of age) meeting inclusion criteria for:

Having a CBC-DIFF performed upon presentation and

Subjects remaining in the hospital (emergency department or in-patient) for at least 12 hours.

The prevalence of sepsis as defined by the Sepsis-2 (ACCP/SCCM 2001 consensus criteria) was 17.8%. This prevalence is higher than the general prevalence of sepsis in emergency department patients; the septic population was likely enriched by the inclusion criteria. The emergency-department population demographics based upon presenting clinical status are summarized in Table 4.

TABLE 4

Emergency department population demographics based on present diagnosis

| Site | Case Control | SIRS | Infection | Sepsis | Total |
| --- | --- | --- | --- | --- | --- |
| 1 | 320 | 111 | 95 | 139 | 665 |
| 2 | 440 | 222 | 60 | 115 | 837 |
| 3 | 328 | 108 | 89 | 131 | 656 |
| Total | 1088 | 441 | 244 | 385 | 2158 |

The subject categories included:
Non-SIRS—case controls, subjects having 0 to 1 SIRS (Systemic Inflammatory Response Syndrome) criteria and no infection
SIRS—subjects having ≥2 SIRS criteria
Infection—subjects having suspected or confirmed infection
Sepsis—subjects having infection plus SIRS
Severe sepsis—subjects having sepsis with one or more organ failure
Septic shock—subjects having sepsis with severe hypotension.

In Table 3, sepsis includes sepsis, severe sepsis, and septic shock.

Samples collected in K2 EDTA were analyzed within two hours of venipuncture. MDW results were compared to the clinical adjudication of sepsis per Sepsis-2 Criteria (defined as a documented or suspected infection together with two or more SIRS criteria). Sepsis criteria had to be met within 12 hours of presentation. Infection diagnosis was determined by retrospective chart review for microbiological, radiological, and molecular results available for up to five to seven days post-emergency-department presentation. Diagnosis was adjudicated at each site by two independent physicians and discordances were arbitrated by a third independent physician.

Table 5 shows the number of samples used in the analysis. The table shows the number of samples with and without sepsis. In addition, for both samples with and without sepsis, the number of samples that had a blast flag or did not have a blast flag was listed. Only 30 of the 2,158 samples (or about 1.39%) of all samples had a blast flag.

TABLE 5

Number of samples

| | | Diagnosis | | |
| --- | --- | --- | --- | --- |
| | | Non-Sepsis | Sepsis | Total |
| Blast | No Flag | 1755 | 373 | 2128 |
| | Flag | 18 | 12 | 30 |
| | Total | 1773 | 385 | 2158 |
| | Flag Percentage | 1.01% | 3.12% | 1.39% |

Figure 9:
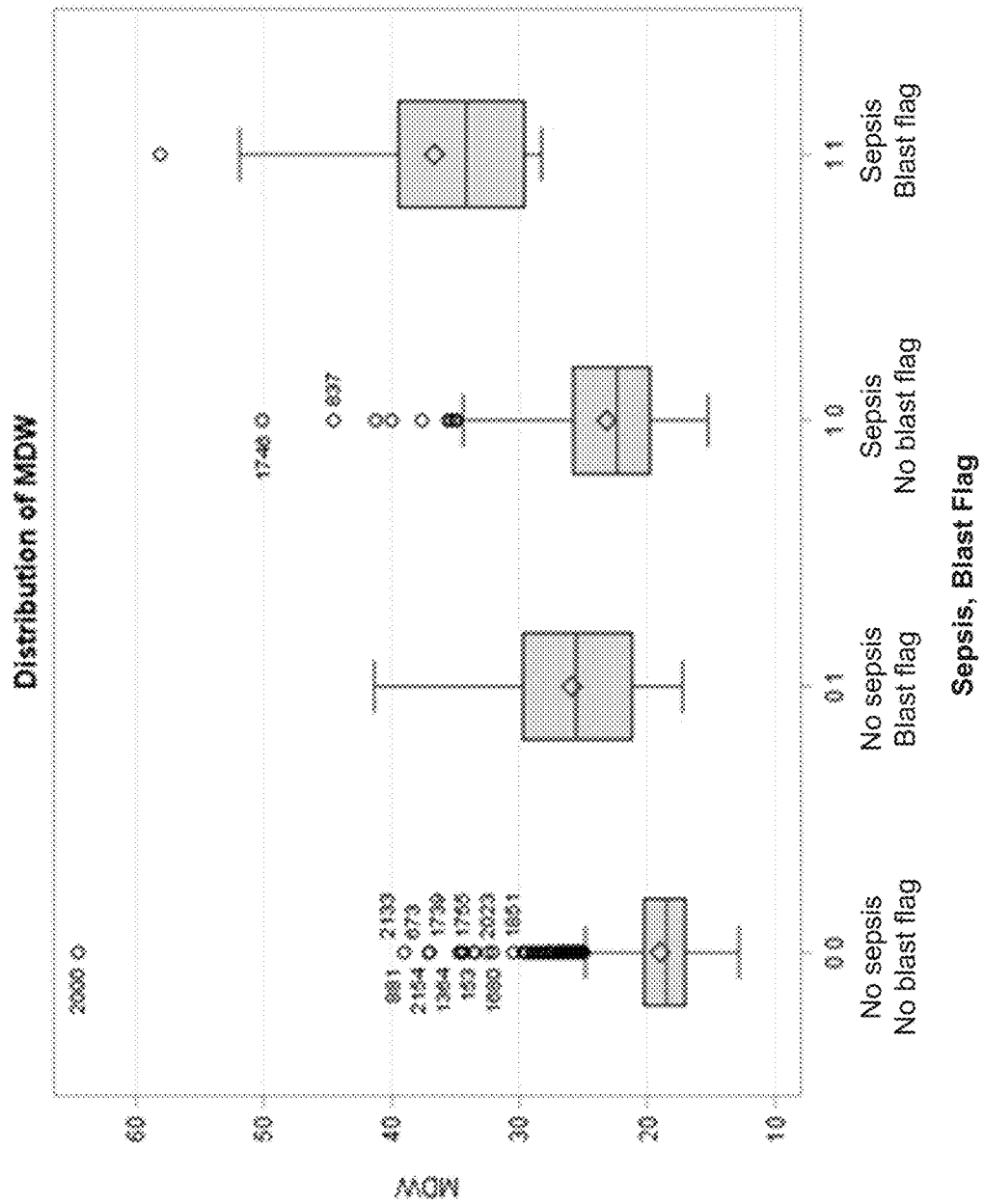
FIG. 9 shows box plots for the distribution of monocyte distribution width (MDW) for blood samples, according to embodiments of the present invention.

FIG. 9 shows box plots for the distribution of monocyte distribution width (MDW) for the samples for four categories (non-sepsis without a blast flag, sepsis without a blast flag, non-sepsis with a blast flag, and sepsis with a blast flag). Table 6 shows the mean monocyte distribution width (MDW) for the samples for the four categories. The MDW for samples with a blast flag is higher than samples without a blast flag for the same sepsis condition.

TABLE 6

MDW means and differences

|  |  | Diagnosis | | |
|---|---|---|---|---|
|  |  | Non-Sepsis | Sepsis | Difference |
| Blast | No Flag | 18.97 | 23.16 | 4.19 |
|  | Flag | 25.90 | 36.68 | 10.78 |
| Difference |  | 6.93 | 13.52 | 6.59 |

Additionally, Table 6 shows the differences in the mean MDW values. With a blast flag, the difference in MDW between non-sepsis and sepsis actually increases. As a result, using MDW to distinguish between non-sepsis and sepsis is unexpectedly possible when the blast flag is present. When the blast flag is present, the MDW increases by an average of 6.93 for non-sepsis samples and by an average of 13.52 for sepsis samples. Note that the MDW for non-sepsis samples with a blast flag is higher than sepsis samples without a blast flag. Hence, if blast flag is not considered in using MDW for evaluating sepsis, non-sepsis samples with the blast flag may be falsely characterized as having sepsis. Although the false positive rate may be acceptable without considering the blast flag, considering the blast flag should improve (reduce) the false positive rate. For some sub-populations, for example, oncology patients, where a relatively high percentage of patients would be expected to have an elevated baseline MDW (i.e., elevated MDW in the absence of infection or sepsis), considering the blast flag may be particularly helpful or even necessary to achieve an acceptable false positive rate.

B. Results Using Blast Flag-Dependent MDW Cutoff Values

Figure 10:
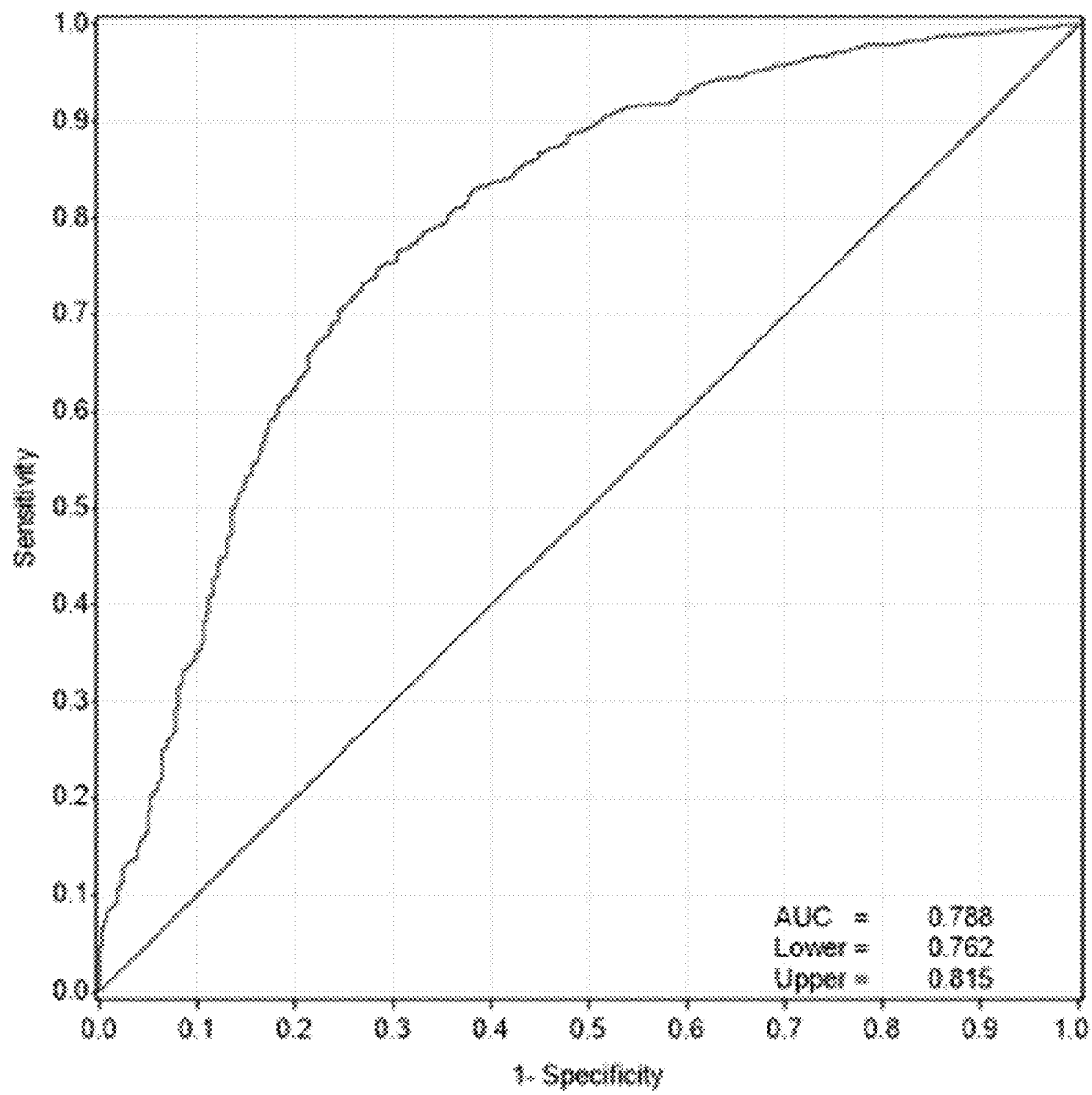
FIG. 10 shows a receiver operating characteristic (ROC) curve for evaluating sepsis status for patients with and without a blast flag, according to embodiments of the present invention.
Figure 11:
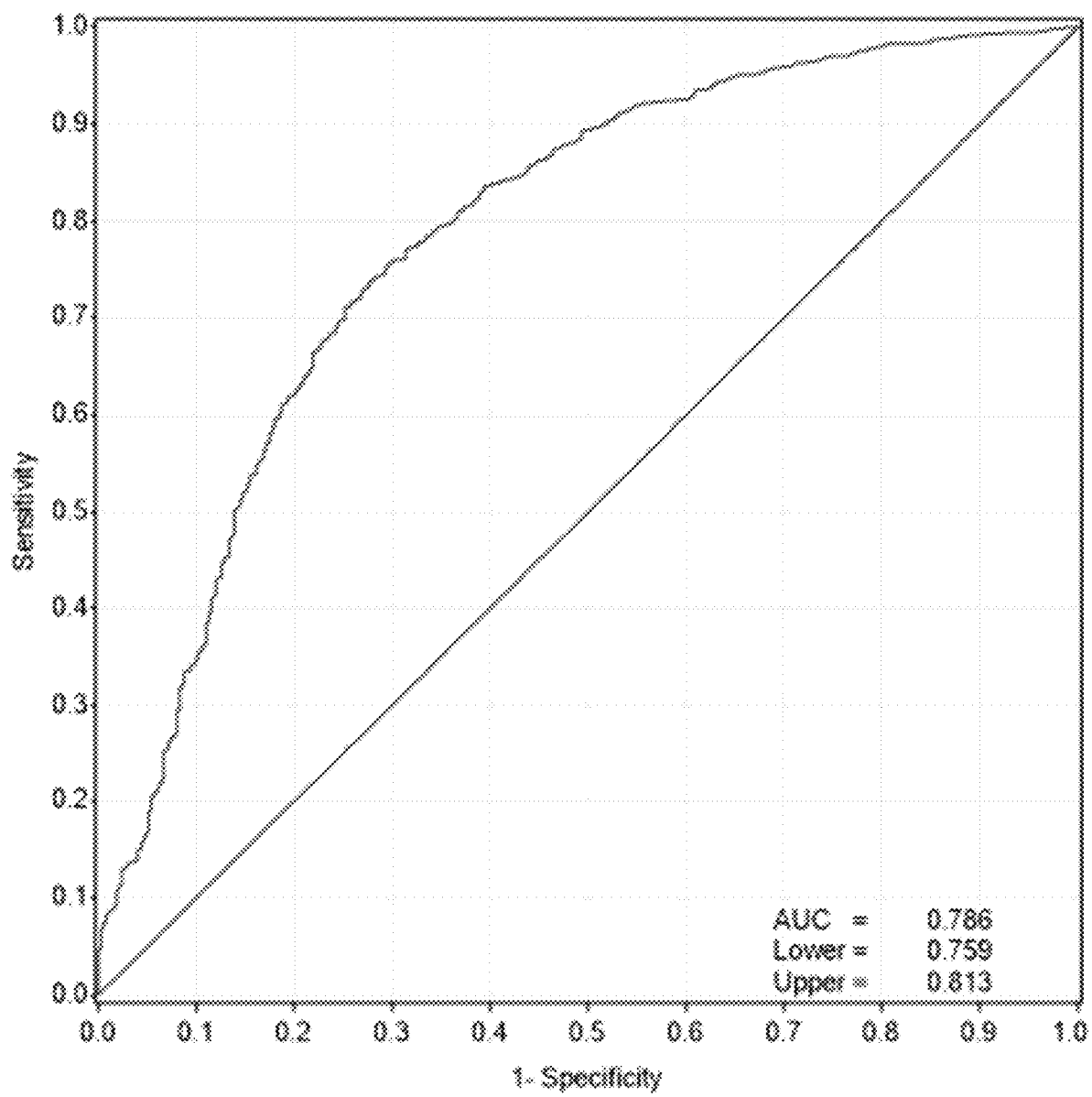
FIG. 11 shows an ROC curve for evaluating sepsis status for patients without a blast flag, according to embodiments of the present invention.
Figure 12:
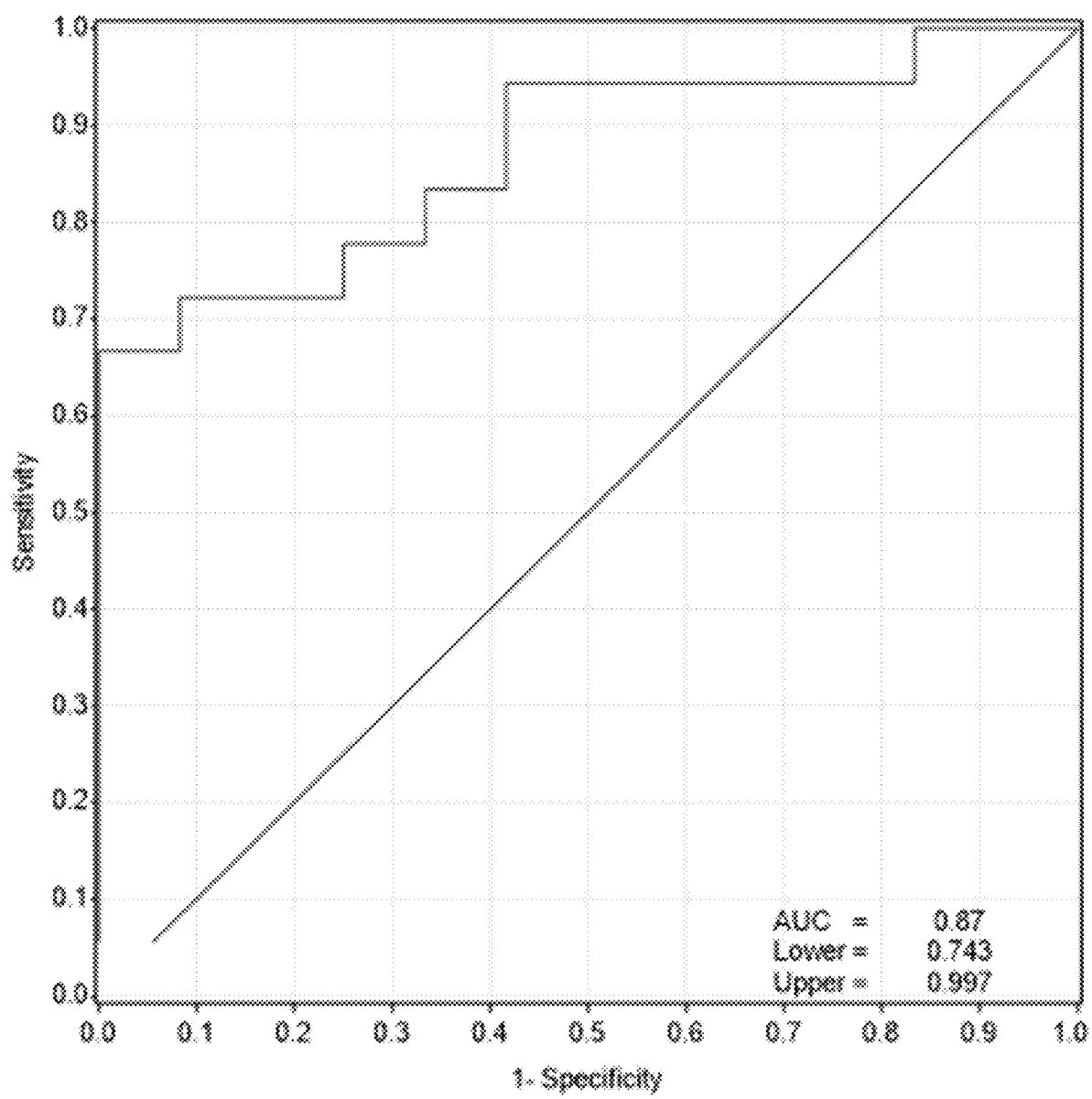
FIG. 12 shows an ROC curve for evaluating sepsis status for patients with a blast flag, according to embodiments of the present invention.
Figure 13:
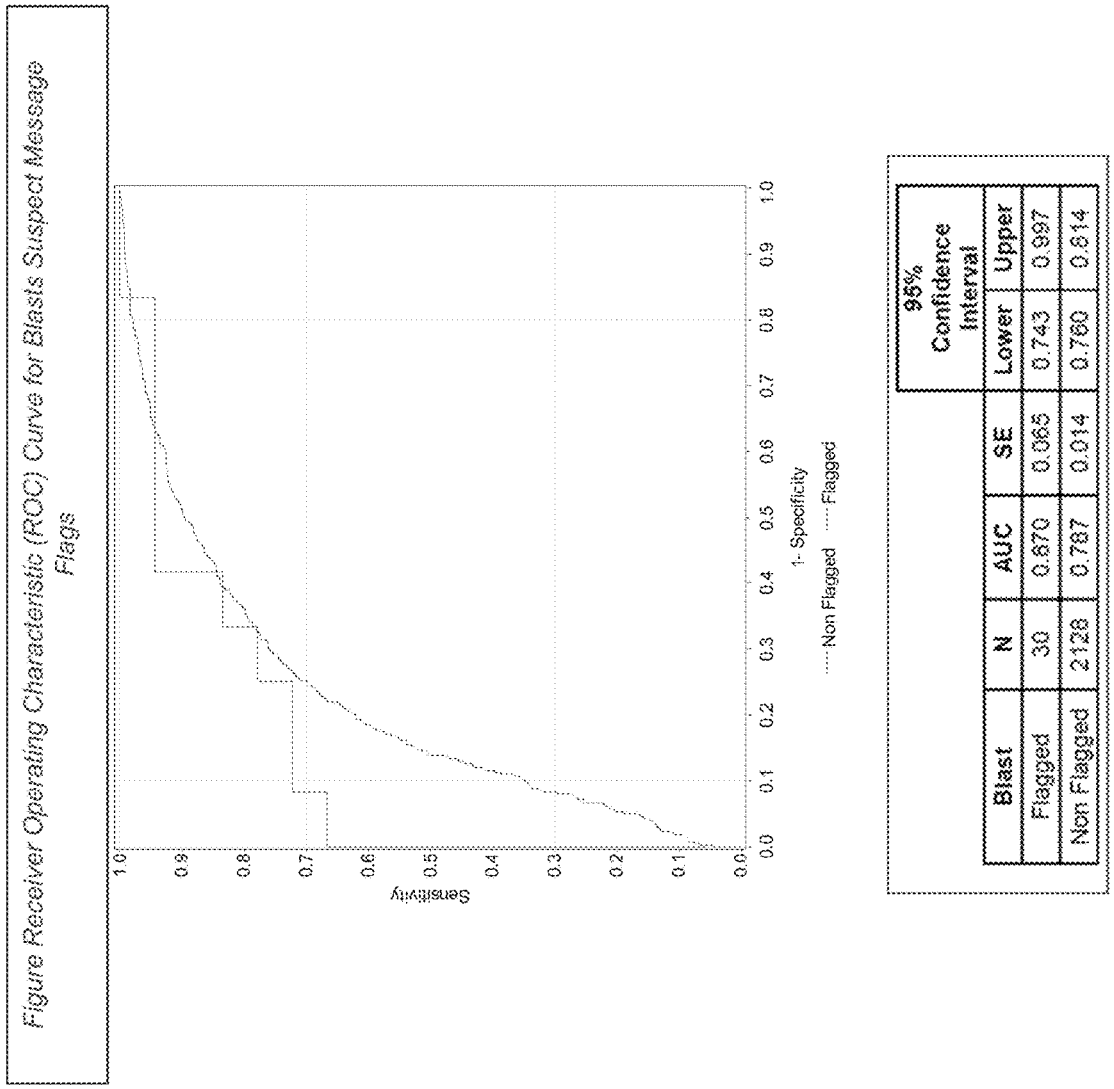
FIG. 13 shows a comparison graph showing ROC for blasts suspect message flags.
Figure 14:
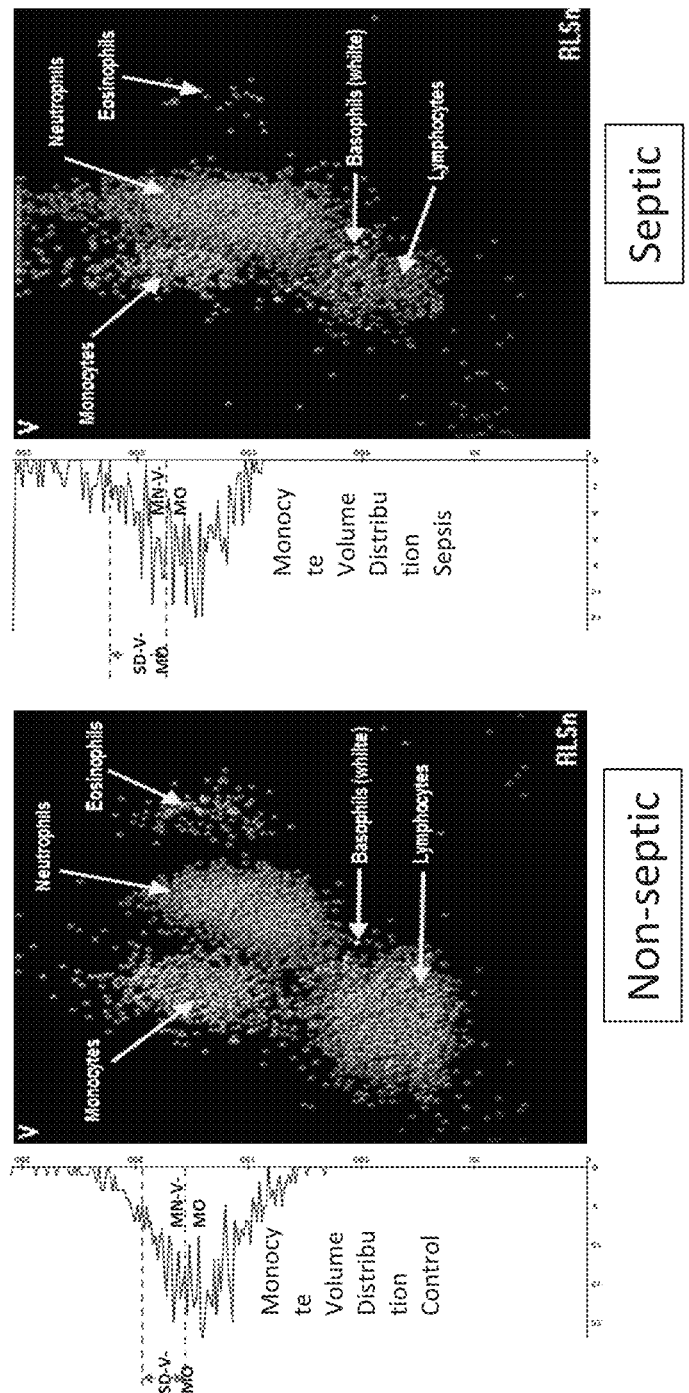
FIG. 14 shows exemplary scatterplots illustrating a comparison between non-septic and septic patients.

An MDW of 20.0 is used as a cutoff value between non-sepsis and sepsis for samples without a blast flag, and an MDW of 29 is used as a cutoff value with a blast flag. FIG. 10 shows the receiver operating characteristic (ROC) curve for all 2,158 patients. The area under the curve was 0.789. FIG. 11 shows the ROC curve for the 2,128 non-blast flagged patients. For the non-blast flagged patients, the area under the curve (AUC) was 0.787. FIG. 12 shows the ROC curve for the 30 blast flagged patients. With the blast flagged patients, the AUC was 0.870. FIG. 13 shows an ROC Curve for comparing blasts suspect message flags between non-flagged and flagged blasts. Table 7 summarizes the AUC, standard error, and 95% confidence limits with using the different blast flag-dependent MDW cutoff values.

TABLE 7

Comparison of AUC

| Population | AUC | Standard Error | 95% Confidence Limits | |
|---|---|---|---|---|
|  |  |  | Lower | Upper |
| All patients | 0.789 | 0.014 | 0.762 | 0.815 |
| Non-blast flagged patients | 0.787 | 0.014 | 0.760 | 0.814 |
| Blast flagged patients | 0.870 | 0.065 | 0.743 | 0.997 |

The results show that using MDW to evaluate sepsis status is possible even when a blast flag is present. In addition, consideration of the blast flag status actually may increase the specificity and sensitivity of the evaluation. The AUC for blast flagged patients increased compared to non-blast flagged patients for this particular data set.

In the preceding description, for the purposes of explanation, numerous details have been set forth in order to provide an understanding of various embodiments of the present technology. It will be apparent to one skilled in the art, however, that certain embodiments may be practiced without some of these details, or with additional details, or in varied combinations or sub-combinations of features of the embodiments.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Additionally, details of any specific embodiment may not always be present in variations of that embodiment or may be added to other embodiments.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the transducer" includes reference to one or more transducers and equivalents thereof known to those skilled in the art, and so forth. The invention has now been described in detail for the purposes of clarity and understanding. However, it will be appreciated that certain changes and modifications may be practice within the scope of the appended claims.

What is claimed is:

1. An automated method for evaluating a sepsis status associated with a blood sample obtained from an individual, the method comprising, through execution of instructions stored on a non-transitory computer readable medium by a processor:

determining a standard deviation of monocyte volume associated with the blood sample, wherein the standard deviation of monocyte volume associated with the blood sample is a standard deviation of volume measurements for individual monocytes in a monocyte population in the blood sample;

determining a blast population characteristic associated with the blood sample;

comparing the blast population characteristic associated with the blood sample to a first cutoff value to provide a first comparison;

determining a second cutoff value based on the first comparison;

comparing the standard deviation of monocyte volume to the second cutoff value to provide a second comparison; and evaluating the sepsis status associated with the blood sample based on the second comparison, wherein evaluating the sepsis status comprises determining the sepsis status as a sepsis status from the group consisting of:
the blood sample does not indicate sepsis; and
the blood sample indicates sepsis.

2. The automated method of claim 1, wherein the blast population characteristic is a binary indicator of the presence or absence of a significant number of blasts.

3. The automated method of claim 1, wherein blast population is identified at least in part based on a size of blasts relative to other white blood cells.

4. The automated method of claim 1, wherein:
the blast population characteristic is a binary parameter,
the blast population characteristic has a first value when there is a probability exceeding a pre-established threshold of a white blood cell population having a blast population that is greater than a highest value in a blast population range for blood samples associated with healthy adults,
the blast population characteristic has a second value when there is not a probability exceeding the pre-established threshold of the white blood cell population having a blast population that is greater than the highest value in the blast population range for blood samples associated with healthy adults, and
the first value is different from the second value.

5. The automated method of claim 1, wherein:
the second cutoff value is higher when the value of the blast population characteristic is greater than or equal to the first cutoff value than when the value of the blast population characteristic is not greater than or equal to the first cutoff value.

6. The automated method of claim 1, further comprising:
determining whether a value of the blast population characteristic is greater than or equal to the first cutoff value,
determining the second cutoff value to be a third cutoff value, and
evaluating the sepsis status as indicating sepsis if the standard deviation of monocyte volume is greater than the second cutoff value, wherein:
the third cutoff value is determined using a first plurality of reference blood samples each having the value of the blast population characteristic greater than or equal to the first cutoff value,
a fourth cutoff value is determined using a second plurality of reference blood samples each having the value of the blast population characteristic neither greater than nor equal to the first cutoff value, and
the third cutoff value is greater than the fourth cutoff value.

7. The automated method of claim 6, wherein:
the third cutoff value is in a range from 26 to 36, and
the fourth cutoff value is in a range from 19 to 23.

8. The automated method of claim 1, further comprising:
determining whether a value of the blast population characteristic is neither greater than nor equal to the first cutoff value,
determining the second cutoff value to be a third cutoff value, and
evaluating the sepsis status as indicating sepsis if the standard deviation of monocyte volume is greater than the second cutoff value, wherein:
the third cutoff value is determined using a second plurality of reference blood samples each having the value of the blast population characteristic neither greater than or equal to the first cutoff value;
a fourth cutoff value is determined using a first plurality of reference blood samples each having the value of the blast population characteristic greater than the first cutoff value; and
the fourth cutoff value is greater than the third cutoff value.

9. The automated method of claim 1, further comprising:
receiving data that the individual has a white blood cell population having a blast population that is greater than a highest value in a blast population range from blood samples associated with healthy adults, wherein the data is not determined from the blood sample, and
determining the second cutoff value based on the received data.

10. The automated method of claim 1, further comprising:
determining a white blood cell count (WBC) associated with the blood sample,
comparing the WBC to a threshold value to provide a third comparison, and
evaluating the sepsis status associated with the blood sample based on the second comparison and the third comparison.

11. The automated method of claim 1, further comprising:
altering a test reporting process based on the evaluation of the sepsis status, or
treating the individual from whom the blood sample was obtained if the sepsis status indicates sepsis.

12. The automated method of claim 1, further comprising:
delivering a hydrodynamically focused stream of the blood sample toward a cell interrogation zone of an optical element; and
measuring, with an electrode assembly, current (DC) impedance of cells of the blood sample passing individually through the cell interrogation zone;
wherein determining the standard deviation of monocyte volume is based on the measured current (DC) impedance of cells of the blood sample.

13. The automated method of claim 1, wherein:
the blast population characteristic indicates a probability exceeding a pre-established threshold of a plurality of white blood cells having a blast population greater than a highest value in a blast population range from blood samples associated with healthy adults.

* * * * *